US007262309B2

(12) United States Patent
Mercep et al.

(10) Patent No.: US 7,262,309 B2
(45) Date of Patent: Aug. 28, 2007

(54) 1- OR 3-THIA-BENZONAPHTHOAZULENES AS INHIBITORS OF TUMOR NECROSIS FACTOR PRODUCTION AND INTERMEDIATES FOR THE PREPARATION THEREOF

(75) Inventors: Mladen Mercep, Zagreb (HR); Milan Mesic, Zagreb (HR); Dijana Pesic, Sibenik (HR); Ivana Ozimec, Trnovec (HR); Rudolf Trojko, Zagreb (HR)

(73) Assignee: GlaxoSmith Kline Istrazivocki Centar Zagreb, D.O.O. (HR)

( * ) Notice: Subject to any disclaimer, the term of this patent is extended or adjusted under 35 U.S.C. 154(b) by 192 days.

(21) Appl. No.: 10/963,979

(22) Filed: Oct. 12, 2004

(65) Prior Publication Data

US 2005/0130964 A1 Jun. 16, 2005

Related U.S. Application Data

(63) Continuation-in-part of application No. PCT/HR03/00014, filed on Apr. 9, 2003.

(30) Foreign Application Priority Data

Apr. 10, 2002 (HR) .......................... P 20020303 A

(51) Int. Cl.
A61K 31/381 (2006.01)
A61K 31/38 (2006.01)
A61K 31/335 (2006.01)
C07D 495/04 (2006.01)

(52) U.S. Cl. ........................ 549/41; 514/431; 514/439; 514/443

(58) Field of Classification Search ................... 549/41
See application file for complete search history.

(56) References Cited

U.S. PATENT DOCUMENTS 3,711,489 A 1/1973 Lombardino
4,198,421 A 4/1980 Cherkofsky et al.

FOREIGN PATENT DOCUMENTS

CA 967573 5/1975
HR 20000310 2/2002
WO WO-01/87890 11/2001

OTHER PUBLICATIONS

Fukawa et al., A Method for Evaluating Analgesic Agents in Rats, J. Pharmacol. Meth., 1980, 4:251-259.
Van Assche and Rutgeerts, Anti-TNF agents in Crohn's disease, Exp. Opin. Invest. Drugs, 2000, 9:103-111.
Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, J. Pharmac. Env. Therap., 1996, 279(3):1453-1461.
Pfeffer et al., Mice Deficient for the 55kd Tumor Necrosis Factor Receptor Are Resistant to Endotixic Shock, yet Succumb to L. monocytogenes Infection, Cell, 1993, 73:457-467.
Keffer et al., Transgenic mice expressing human tumour necrosis factor: a predictive genetic model of arthritis, EMBO J., 1991, 10:4025-4031.
Tsuji et al., Studies on Anti-Inflammatory Agents. VI. Synthesis and Pharmacological Properties of 2,3-Diarylthiophenes, Chem. Pharm. Bull., 1998, 46(2):279-286.
Ueda et al., The Synthesis of 10-(4-Methylpiperazino)dibenzo[b,f]thiepin and Related Compounds. Neurotrpic and Psychotropic Agents, Chem. Pharm. Bull., 1975, 23(10):2223-2231.
Koplcova and Protiva, Synthesis of 7-(4-methylpiperazino)-7,8-dihydrobenzo[b]naphtho[2,1-f]thiepin and of Related Compunds, Collect. Czech. Chem. Commun., 1974, 39:3147-3152.
Georgopoulos et al., Transmembrane TNF Is Sufficient To Induce Localized Tissue Toxicity and Chronic Inflammatory Arthritis in Transgenic Mice, J. Inflamm., 1996, 46:86-97.
Bresnihan, Treatment with Recombinant Human Interleukin-1 Receptor Antagonist (rhIL-1ra) in Rheumatoid Arthritis (RA); Results of a Randomized Double-Blind, Placebo-Controlled Multicenter trial, Arthrit. Rheum., 1996, 39:73.
Mori et al., Attenuation of Collagen-Induced Arthritis in 55-kDa TNF Receptor Type 1 (TNFR1)-IgG1-Treated and TNFR1-Deficient Mice, J. Immunol., 1996, 157:3178-3182.
Elliott et al., Randmoised double-blind comparison of chimeric monoclonal antibody to tumor necrosis factor alpha (cA2) versus placebo in rheumatoid arthritis, The Lancet, 1994, 344:1105-1110.
Carswell et al., An endotoxin-induced serum factor that causes necrosis of tumors, Proc. Natl. Acad. Sci. U.S.A., 1975, 72:3666-3670.
Kopicova et al., Potential Tetracyclic Neuroleptics: 12-(4-methylpiperazino)benzo[b]naphtho[2,3-f]theipin and its 12,13-dihydro Derivative, Collect. Czech. Chem. Commun., 1975. 40:1960-1965.
Schweizer et al., Combined automated writhing/motility test for testing analgesics, Agents and Actions, 1988, 23:29-31.
Collier et al., The Abdominal Constriction Response and its Suppression By Analgesic Drugs in the Mouse, Br. J. Pharmac. Chemother., 1968, 32:295-310.
Nyiondi-Bonguen et al., [4+2]—Cycloadditions of 3-Amino-4-imino-4H-thieno[3,4-c][1]benzopyran with some Selected Dienophiles, J. Chem Soc., Perkin Trans. 1, 1994, 15:2191-2195.
Mattioli and Ghia, omega-Dialkylaminoalkyl Ethers of Phenyl-(5-substituted 1-phenyl-1H-pyrazol-4-yl)methanols with Analgesic and Anti-Inflammatory Activity, J. Heterocyclic Chem., 1997, 34:963-968.
Dinarello, Interleukin-1, Rev. Infect Disease, 1984, 6(1):51-95.
Dinarello, An Update on Human Interleukin-1: From Molecular Biology to Clinical Relevance, J. Clinical Immunology, 1985, 5:287-297.
Cagniant and Kirsch, C.R. Acad., Sc., 1976, 283:683-686.

*Primary Examiner*—Laura L. Stockton
(74) *Attorney, Agent, or Firm*—J. Scott Young

(57) ABSTRACT

The present invention relates to benzonaphthoazulene derivatives of tiophene class, to their pharmacologically acceptable salts and solvates, to processes and intermediates for the preparation thereof as well as to their antiinflammatory effects, especially to the inhibition of tumor necrosis factor-α (TNF-α) production and the inhibition of interleukin-1 (IL-1) production as well as to their analgetic action.

12 Claims, No Drawings

1- OR 3-THIA-BENZONAPHTHOAZULENES AS INHIBITORS OF TUMOR NECROSIS FACTOR PRODUCTION AND INTERMEDIATES FOR THE PREPARATION THEREOF

CROSS-REFERENCE TO PRIOR APPLICATIONS

This is a continuation-in-part of International Patent Application No. PCT/HR03/00014 filed Apr. 9, 2003, and claims the benefit of Croatian Patent Application No. P20020303A, filed Apr. 10, 2002, which is incorporated by reference herein. The International Application was published in English on Oct. 16, 2003 as WO 2003/084961 A1 under PCT Article 21(2).

TECHNICAL FIELD

The present invention relates to benzonaphthoazulene derivatives of tiophene class, to their pharmacologically acceptable salts and solvates, to processes and intermediates for the preparation thereof as well as to their antiinflammatory effects, especially to the inhibition of tumour necrosis factor-α (TNF-α) production and the inhibition of interleukin-1 (IL-1) production as well as to their analgetic action.

PRIOR ART

Some 1,3-diaza-dibenzoazulene derivatives and salts thereof are well-known as a novel class of compounds having an antiinflammatory action (U.S. Pat. No. 3,711,489, U.S. Pat. No. 4,198,421 and CA 967,573). In the literature, from the class of 1-thia-dibenzoazulenes there are disclosed derivatives substituted in 2-position with methyl, methylketone, nitro group or with carboxylic group derivatives (Cagniant P G, *C. R. Hebd. Sceances Acad. Sci.*, 1976, 283:683-686), and 1-thia-dibenzoazulene derivatives having alkyloxy substituents in 2-position (WO 01/878990), which also possess a strong antiinflammatory action.

Well-known are also some benzonaphthoazulenes of the thiophene class such as 9,14-dihydro-9,14-dioxo-8-oxa-1-thia-benzo[e]naphtho[3,2-h]azulenes, wherein 3-position is substituted by a cyano group and in 2-position there may be amine, urea or acetamide as a substituent (Nyiondi-Bonguen E et al., *J. Chem. Soc., Perkin Trans.* 1, 1994, 15:2191-2195). However, according to our knowledge and to available literature data, benzonaphthoazulenes of thiophene class of the present invention are not known. It is also not known that such compounds could possess an antiinflammatory action as inhibitors of TNF-α secretion and inhibitors of IL-1 secretion as well as an analgetic action. In 1975 TNF-α was defined as a serum factor induced by endotoxin and causing tumour necrosis in vitro and in vivo (Carswell E A et al., *Proc. Natl. Acad. Sci. U.S.A.,* 1975, 72:3666-3670). Besides an antitumour action, TNF-α also possesses numerous other biological actions important in the homeostasis of organisms and in pathophysiological conditions. The main sources of TNF-α are monocytes-macrophages, T-lymphocytes and mastocytes.

The discovery that anti-TNF-α antibodies (cA2) have an action in treating patients with rheumatoid arthritis (RA) (Elliott M et al., *Lancet,* 1994, 344:1105-1110) led to an increased interest in finding novel TNF-α inhibitors as possible potent drugs for RA. Rheumatoid arthritis is an autoimmune chronic inflammatory disease characterized by irreversible pathological changes in the joints. Besides in RA, TNF-α antagonists may also be used in numerous pathological conditions and diseases such as spondylitis, osteoarthritis, gout and other arthritic conditions, sepsis, septic shock, toxic shock syndrom, atopic dermatitis, contact dermatitis, psoriasis, glomerulonephritis, lupus erythematosus, scleroderma, asthma, cachexia, chronic obstructive lung disease, congestive cardiac arrest, insulin resistance, lung fibrosis, multiple sclerosis, Crohn's disease, ulcerative colitis, viral infections and AIDS.

Evidence for the biological importance of TNF-α was obtained by in vivo experiments in mice, in which mice gens for TNF-α or its receptor were inactivated. Such animals are resistant to collagen-induced arthritis (Mori L et al., *J. Immunol.,* 1996, 157:3178-3182) and to endotoxin-caused shock (Pfeffer K et al., *Cell,* 1993, 73:457-467). In animal assays where TNF-α level was increased, a chronic inflammatory polyarthritis occured (Georgopoulos S et al., *J. Inflamm.,* 1996, 46:86-97; Keffer J et al., *EMBO J.,* 1991, 10:4025-4031) and its pathological picture was alleviated by inhibitors of TNF-α production. The treatment of such inflammatory and pathological conditions usually includes the application of non-steroid antiinflammatory drugs and, in more severe cases, gold salts, D-penicillinamine or methotrexate are administered. Said drugs act symptomatically, but they do not stop the pathological process. Novel approaches in the therapy of rheumatoid arthritis are based upon drugs such as tenidap, leflunomide, cyclosporin, FK-506 and upon biomolecules neutralizing the TNF-α action. At present there are commercially available etanercept (Enbrel, Immunex/Wyeth), a fusion protein of the soluble TNF-α receptor, and infliximab (Remicade, Centocor), a chimeric monoclonal human and mouse antibody. Besides in RA therapy, etanercept and infliximab are also registered for the therapy of Crohn's disease (*Exp. Opin. Invest. Drugs,* 2000, 9:103).

In RA therapy, besides inhibition of TNF-α secretion, also the inhibition of IL-1 secretion is very important since IL-1 is an important cytokin in cell regulation and immunoregulation as well as in pathophysiological conditions such as inflammation (Dinarello C A et al., *Rev. Infect. Disease,* 1984, 6:51). Well-known biological activities of IL-1 are: activation of T-cells, induction of elevated temperature, stimulation of secretion of prostaglandine or collagenase, chemotaxia of neutrophils and reduction of iron level in plasma (Dinarello C A, *J. Clinical Immunology,* 1985, 5:287). Two receptors to which IL-1 may bind are well-known: IL-1RI and IL-1RII. Whereas IL-1RI transfers a signal intracellularly, IL-1RII is situated on the cell surface and does not transfer a signal inside the cell. Since IL1-RII binds IL-1 as well as IL1-RI, it may act as a negative regulator of IL-1 action. Besides this mechanism of signal transfer regulation, another natural antagonist of IL-1 receptor (IL-1ra) is present in cells. This protein binds to IL-1RI but does not transfer any signal. However, its potency in stopping the signal transfer is not high and its concentration has to be 500 times higher than that of IL-1 in order to achieve a break in the signal transfer. Recombinant human IL-1ra (Amgen) was clinically tested (Bresnihan B et al., *Arthrit. Rheum.,* 1996, 39:73) and the obtained results indicated an improvement of the clinical picture in 472 RA patients over an placebo. These results indicate the importance of the inhibition of IL-1 action in treating diseases such as RA where IL-1 production is disturbed.

Since there exists a synergistic action of TNF-α and IL-1, benzonaphthoazulenes may be used in treating conditions and diseases related to an enhanced secretion of TNF-α and IL-1.

Inventive Solution

The present invention relates to benzonaphthoazulenes of the formula I

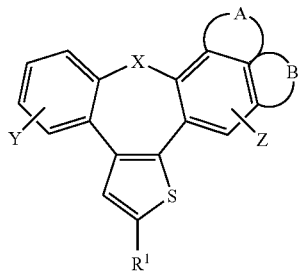

I wherein

X may be CH$_2$ or a hetero atom such as O, S, S(=O), S(=O)$_2$, or NR$^a$, wherein R$^a$ is hydrogen or a protecting group;

Y and Z independently from each other denote one or more identical or different substituents linked to any available carbon atom, and may be hydrogen, halogen, C$_1$-C$_4$ alkyl, C$_2$-C$_4$ alkenyl, C$_2$-C$_4$ alkinyl, trifluoromethyl, halo-C$_1$-C$_4$ alkyl, hydroxy, C$_1$-C$_4$ alkoxy, trifluoromethoxy, C$_1$-C$_4$ alkanoyl, amino, amino-C$_1$-C$_4$ alkyl, C$_1$-C$_4$ alkylamino, N-(C$_1$-C$_4$-alkyl)amino, N,N-di(C$_1$-C$_4$-alkyl)amino, thiol, C$_1$-C$_4$ alkylthio, sulfonyl, C$_1$-C$_4$ alkylsulfonyl, sulfinyl, C$_1$-C$_4$ alkylsulfinyl, carboxy, C$_1$-C$_4$ alkoxycarbonyl, nitro;

G$_A$ or G$_B$:

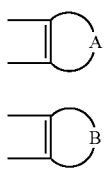

G$_A$

G$_B$ independently from each other denote one or more identical or different substituents linked to any available carbon atom, and may be halogen, C$_1$-C$_4$ alkyl, C$_2$-C$_4$ alkenyl, C$_2$-C$_4$ alkinyl, trifluoromethyl, halo-C$_1$-C$_4$ alkyl, hydroxy, C$_1$-C$_4$ alkoxy, trifluoromethoxy, C$_1$-C$_4$ alkanoyl, amino, amino-C$_1$-C$_4$ alkyl, C$_1$-C$_4$ alkylamino, N-(C$_1$-C$_4$-alkyl)amino, N,N-di(C$_1$-C$_4$-alkyl)amino, thiol, C$_1$-C$_4$ alkylthio, sulfonyl, C$_1$-C$_4$ alkylsulfonyl, sulfinyl, C$_1$-C$_4$ alkylsulfinyl, carboxy, C$_1$-C$_4$ alkoxycarbonyl, nitro;

R$^1$ may be halogen, an optionally substituted C$_1$-C$_7$ alkyl or C$_2$-C$_7$ alkenyl, C$_2$-C$_7$ alkinyl, an optionally substituted aryl or heteroaryl and a heterocycle, hydroxy, hydroxy-C$_2$-C$_7$ alkenyl, hydroxy-C$_2$-C$_7$ alkinyl, C$_1$-C$_7$ alkoxy, thiol, thio-C$_2$-C$_7$ alkenyl, thio-C$_2$-C$_7$ alkinyl, C$_1$-C$_7$ alkylthio, amino-C$_1$-C$_7$ alkyl, amino-C$_2$-C$_7$ alkenyl, amino-C$_2$-C$_7$ alkinyl, amino-C$_1$-C$_7$ alkoxy, C$_1$-C$_7$ alkanoyl, aroyl, oxo-C$_1$-C$_7$ alkyl, C$_1$-C$_7$ alkanoyloxy, carboxy, an optionally substituted C$_1$-C$_7$ alkyloxycarbonyl or aryloxycarbonyl, carbamoyl, N-(C$_1$-C$_7$-alkyl)carbamoyl, N,N-di(C$_1$-C$_7$-alkyl)carbamoyl, cyano-C$_1$-C$_7$ alkyl, sulfonyl, C$_1$-C$_7$ alkylsulfonyl, sulfinyl, C$_1$-C$_7$ alkylsulfinyl, nitro, or a substituent of the formula II

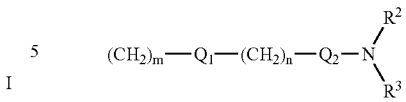

II wherein

R$^2$ and R$^3$ simultaneously or independently from each other may be hydrogen, C$_1$-C$_4$ alkyl, aryl or together with N have the meaning of an optionally substituted heterocycle or heteroaryl;

n represents an integer from 0 to 3;

m represents an integer from 1 to 3;

Q$_1$ and Q$_2$ represent, independently from each other, oxygen, sulfur or groups:

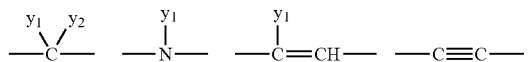

wherein the substituents y$_1$ and y$_2$ independently from each other may be hydrogen, halogen, an optionally substituted C$_1$-C$_4$ alkyl or aryl, hydroxy, C$_1$-C$_4$ alkoxy, C$_1$-C$_4$ alkanoyl, thiol, C$_1$-C$_4$ alkylthio, sulfonyl, C$_1$-C$_4$ alkylsulfonyl, sulfinyl, C$_1$-C$_4$ alkylsulfinyl, nitro or together form carbonyl or imino group;

as well as to pharmacologically acceptable salts and solvates thereof.

Preferred are compounds, wherein X has the meaning of S or O; Y and Z have the meaning of H; R$^1$ has the meaning of CO$_2$Et, CH$_2$OH; R$^1$ has the meaning of the formula II; the symbol m has the meaning of 1, n has the meaning of 1 or 2, Q$_1$ has the meaning of O and Q$_2$ has the meaning of CH$_2$; R$^2$ and/or R$^3$ have the meaning of H, CH$_3$ or together with N the meaning of morpholine-4-yl, piperidine-1-yl or pyrrolidine-1-yl; G$_A$ or G$_B$ have the meaning of structures

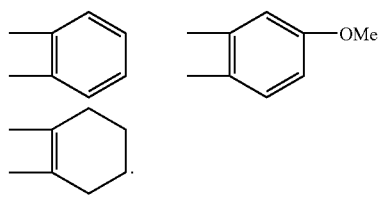

The term "halo", "hal" or "halogen" relates to a halogen atom which may be fluorine, chlorine, bromine or iodine.

The term "alkyl" relates to alkyl groups with the meaning of alkanes wherefrom radicals are derived, which radicals may be straight, branched or cyclic or a combination of straight and cyclic ones and branched and cyclic ones. The preferred straight or branched alkyls are e.g. methyl, ethyl, propyl, isopropyl, butyl, sec-butyl and tert-butyl. The preferred cyclic alkyls are e.g. cyclopentyl or cyclohexyl.

The term "haloalkyl" relates to alkyl groups which must be substituted with at least one halogen atom. The most frequent haloalkyls are e.g. chloromethyl, dichloromethyl, trifluoromethyl or 1,2-dichloropropyl.

The term "alkenyl" relates to alkenyl groups having the meaning of hydrocarbon radicals, which may be straight, branched or cyclic or are a combination of straight and cyclic ones or branched and cyclic ones, but having at least one carbon-carbon double bond. The most frequent alkenyls are ethenyl, propenyl, butenyl or cyclohexenyl.

The term "alkinyl" relates to alkinyl groups having the meaning of hydrocarbon radicals, which are straight or branched and contain at least one and at most two carbon-carbon triple bonds. The most frequent alkinyls are e.g. ethinyl, propinyl or butinyl.

The term "alkoxy" relates to straight or branched chains of alkoxy group. Examples of such groups are methoxy, propoxy, prop-2-oxy, butoxy, but-2-oxy or methylprop-2-oxy.

The term "aryl" relates to groups having the meaning of an aromatic ring, e.g. phenyl, as well as to fused aromatic rings. Aryl contains one ring with at least 6 carbon atoms or two rings with totally 10 carbon atoms and with alternating double (resonant) bonds between carbon atoms. The most freqently used aryls are e.g. phenyl or naphthyl. In general, aryl groups may be linked to the rest of the molecule by any available carbon atom via a direct bond or via a $C_1$-$C_4$ alkylene group such as methylene or ethylene.

The term "heteroaryl" relates to groups having the meaning of aromatic and partially aromatic groups of a monocyclic or bicyclic ring with 4 to 12 carbon atoms, at least one of them being a hetero atom such as O, S or N, and the available nitrogen atom or carbon atom is the binding site of the group to the rest of the molecule either via a direct bond or via a $C_1$-$C_4$ alkylene group defined earlier. Examples of this type are thiophenyl, pyrrolyl, imidazolyl, pyridinyl, oxazolyl, thiazolyl, pyrazolyl, tetrazolyl, pirimidinyl, pyrazinyl, quinolinyl or triazinyl.

The term "heterocycle" relates to five-member or six-member, fully saturated or partly unsaturated heterocyclic groups containing at least one hetero atom such as O, S or N, and the available nitrogen atom or carbon atom is the binding site of the group to the rest of the molecule either via a direct bond or via a $C_1$-$C_4$ alkylene group defined earlier. The most frequent examples are morpholinyl, piperidinyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The term "optionally substituted alkyl" relates to alkyl groups which may be optionally additionally substituted with one, two, three or more substituents. Such substituents may be halogen atom (preferably fluorine or chlorine), hydroxy, $C_1$-$C_4$ alkoxy (preferably methoxy or ethoxy), thiol, $C_1$-$C_4$ alkylthio (preferably methylthio or ethylthio), amino, N-($C_1$-$C_4$) alkylamino (preferably N-methylamino or N-ethylamino), N,N-di($C_1$-$C_4$-alkyl)-amino (preferably dimethylamino or diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

The term "optionally substituted alkenyl" relates to alkenyl groups optionally additionally substituted with one, two or three halogen atoms. Such substituents may be e.g. 2-chloroethenyl, 1,2-dichloroethenyl or 2-bromo-propene-1-yl.

The term "optionally substituted aryl, heteroaryl or heterocycle" relates to aryl, heteroaryl or heterocyclic groups which may be optionally additionally substituted with one or two substituents. The substituents may be halogen (preferably chlorine or fluorine), $C_1$-$C_4$ alkyl (preferably methyl, ethyl or isopropyl), cyano, nitro, hydroxy, $C_1$-$C_4$ alkoxy (preferably methoxy or ethoxy), thiol, $C_1$-$C_4$ alkylthio (preferably methylthio or ethylthio), amino, N-($C_1$-$C_4$) alkylamino (preferably N-methylamino or N-ethylamino), N,N-di($C_1$-$C_4$-alkyl)-amino (preferably N,N-dimethylamino or N,N-diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

When X has the meaning of $NR^a$ and $R^a$ has the meaning of a protecting group, then $R^a$ relates to groups such as alkyl (preferably methyl or ethyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).

When $R^2$ and $R^3$ together with N have the meaning of heteroaryl or heterocycle, this means that such heteroaryls or heterocycles have at least one carbon atom replaced by a nitrogen atom through which the groups are linked to the rest of the molecule. Examples of such groups are morpholine-4-yl, piperidine-1-yl, pyrrolidine-1-yl, imidazole-1-yl or piperazine-1-yl.

The term "pharmaceutically suitable salts" relates to salts of the compounds of the formula I and include e.g. salts with $C_1$-$C_4$ alkylhalides (preferably methyl bromide, methyl chloride) (quaternary ammonium salts), with inorganic acids (hydrochloric, hydrobromic, phosphoric, metaphosphoric, nitric or sulfuric acids) or with organic acids (tartaric, acetic, citric, maleic, lactic, fumaric, benzoic, succinic, methane sulfonic or p-toluene sulfonic acids).

Some compounds of the formula I may form salts with organic or inorganic acids or bases and these are also included in the present invention.

Solvates (most frequently hydrates) which may form compounds of the formula I or salts thereof are also an object of the present invention.

Depending upon the nature of particular substituents, the compounds of the formula I may have geometric isomers and one or more chiral centres so that there can exist enantiomers or diastereoisomers. The present invention also relates to such isomers and mixtures thereof, including racemates.

The present invention also relates to all possible tautomeric forms of particular compounds of the formula I.

A further object of the present invention relates to the preparation of compounds of the formula I according to processes comprising a) for compounds of the formula I, wherein $R^1$ is alkyloxycarbonyl,
a cyclisation of the compound of the formula III

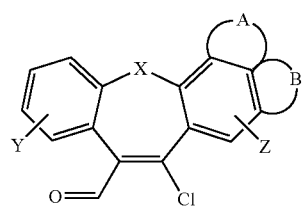

III with esters of mercaptoacetic acid;

b) for compounds of the formula I, wherein $Q_1$ has the meaning of —O—,
a reaction of alcohols of the formula V

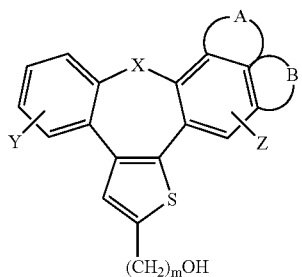

(CH$_2$)$_m$OH with compounds of the formula IV

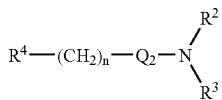

wherein R$^4$ has a meaning of a leaving group;

c) for the compounds of the formula I, wherein Q$_1$ has a meaning of —O—, —NH—, —S— or —C≡C—, reaction of the compounds of the formula Va

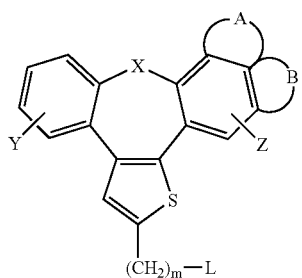

(CH$_2$)$_m$—L wherein L has a meaning of a leaving group, with compounds of the formula IVa

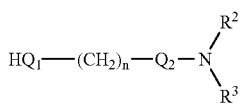

d) for the compounds of the formula I, wherein Q$_1$ has a meaning of a hetero atom —O—, —NH— or —S—, a reaction of the compounds of the formula Vb

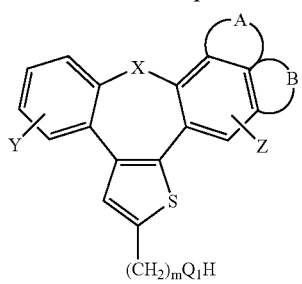

(CH$_2$)$_m$Q$_1$H with the compounds of the formula IV, wherein R$^4$ has a meaning of a leaving group;

e) for the compounds of the formula I, wherein Q$_1$, has a meaning of —C=C—, a reaction of the compounds of the formula Vb, wherein Q$_1$ has a meaning of carbonyl, with phosphorous ylides.

Preparation Methods:

a) Cyclization of the compounds of the formula III with ethyl mercaptoacetate is carried out by methods disclosed for the preparation of analogous compounds. The reaction is carried out in the presence of organic bases (preferably pyridine) at the boiling point during 1 to 5 hours. The obtained tetracyclic products may be isolated by column chromatography or by recrystallization from an appropriate solvent.

The starting substances for the preparation of the compounds of the formula III, ketones of the formula VI,

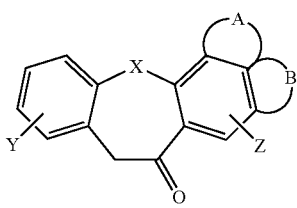

are already known or are prepared by methods disclosed for the preparation of analogous compounds. Thus e.g. the compounds of the formula VI may be obtained starting from compounds of the formula VIII

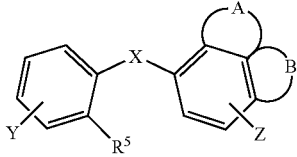

wherein R$^5$ has a meaning of a CO$_2$H group, in such a way that by suitable chemical transformations there is obtained a compound of the formula VIII wherein R$^5$ has the meaning of CH$_2$CO$_2$H. By the action of polyphosphoric acid, cyclization and formation of a ketone of the formula VI occur. A similar reaction sequence has been disclosed earlier in Protiva M et al. (CS 163583, *Collect. Czech. Chem. Commun.*, 1975, 40:1960-1965 and *Collect. Czech. Chem. Commun.*, 1974, 39:3147-3152). Alternatively, the compound of the formula VIII, wherein R$^5$ has the meaning of CH$_2$CO$_2$H, may be prepared by reacting the compound of the formula VIII, wherein R$^5$ is COCH$_3$, with sulfur and morpholine and by hydrolyzing thioamide thus obtained (Ueda I et al., *Chem. Pharm. Bull.*, 1975, 23:2223-2231). By the action of Vilsmeier-Haack reagent upon the corresponding ketones of the formula VI, compounds of the formula III (Tsuji K et al., *Chem. Pharm. Bull.*, 1998, 46:279-286) are prepared.

b) Compounds of the formula I according to the present process may be prepared by reaction of alcohols of the formula V and compounds of the formula IV, wherein R$^4$ has the meaning of a leaving group, which may be a halogen atom (most frequently bromine, iodine or chlorine) or sulfonyloxy group (most frequently trifluoromethylsulfonyloxy or p-toluenesulfonyloxy). The reaction of condensation may be carried out according to methods disclosed for the preparation of analogous compounds (Menozzi G et al., *J. Heterocyclic Chem.*, 1997, 34:963-968 or WO 01/87890). The reaction is carried out at a temperature from 20° C. to 100° C. during 1 to 24 hours in a two-phase system (preferably with 50% NaOH/toluene) in the presence of a phase transfer catalyst (preferably benzyl triethyl ammonium chloride, benzyl triethyl ammonium bromide, cetyl trimethyl bromide).

After treating the reaction mixture, the products formed are isolated by recrystallization or chromatography on a silica gel column.

The starting substances, alcohols of the formula V, may be prepared from the compounds of the formula I, wherein $R^1$ has the meaning of a suitable functional group. Thus e.g. alcohols of the formula V may be obtained by the reduction of alkyloxycarbonyl group (e.g. ethyloxycarbonyl) by using metal hydrides such as lithium aluminum hydride or sodium borohydride. Further, alcohols of the formula V may be prepared by hydrolysis of the corresponding esters in an alkaline or acidic medium.

The starting compounds of the formula IV are already known or are prepared according to methods disclosed for the preparation of analogous compounds.

c) Compounds of the formula I according to the present process may be prepared by reacting compounds of the formula Va, wherein L has the meaning of a leaving group defined earlier for $R^4$, and compounds of the formula IVa, wherein $Q_1$ has the meaning of oxygen, nitrogen, sulfur or —C≡C—. The most suitable condensation reactions are reactions of nucleophilic substitution on a saturated carbon atom as disclosed in the literature.

The starting compounds of the formula Va (most frequently halides) may be obtained by halogenation (e.g. bromination or chlorination) of alcohols of the formula V with the usual halogenating agents (e.g. hydrobromic acid, $PBr_3$, $SOCl_2$ or $PCl_5$) by processes as disclosed in the literature. The obtained compounds may be isolated or may be used without isolation as suitable intermediates for the preparation of the compounds of the formula I.

The starting compounds of the formula IVa are already known or are prepared according to methods disclosed for the preparation of analogous compounds.

d) The compounds of the formula I, wherein $Q_1$ has a meaning of —O—, —NH— or —S—, may be prepared by condensation of the compounds of the formula Vb and of compounds of the formula IV, wherein $R^4$ has the meaning of a leaving group defined earlier. The reaction may be carried out at reaction conditions disclosed in method b) or by reactions of nucleophilic substitution disclosed in the literature. The starting alcohols, amines and thiols may be obtained by a reaction of water, ammonia or hydrogen sulfide with compounds Va according to processes disclosed in the literature.

e) The alcohols of the structure V may be oxidized to corresponding compounds of the formula Vb, wherein $Q_1$ has the meaning of carbonyl and which may further, by reaction with corresponding ylide reagents, result in a prolongation of the chain and in the formation of an alkenyl substituent with carbonyl or ester groups as disclosed in HR patent application No. 20000310.

Besides the reactions mentioned above, the compounds of the formula I may be prepared by transforming other compounds of the formula I and it is to be understood that the present invention also comprises such compounds and processes. A special example of a change of a functional group is the reaction of the aldehyde group with chosen phosphorous ylides resulting in a prolongation of the chain and the formation of an alkenyl substituent with carbonyl or ester groups as disclosed in HR patent application No. 20000310. These reactions are carried out in solvents such as benzene, toluene or hexane at elevated temperature (most frequently at boiling temperature).

By reacting the compounds of the formula Va with 1-alkyne in an alkaline medium (such as sodium amide in ammonia) the compounds of the formula I, wherein $Q_1$ is —C≡C—, are obtained. The reaction conditions of this process are disclosed in the literature. At similar reaction conditions (nucleophilic substitution) various ether, thioether or amine derivatives may be prepared.

The formylation of the compounds of the formula I by processes such as e.g. Vilsmeier acylation or reaction of n-BuLi and N,N-dimethylformamide is a further general example of a transformation. The reaction conditions of these processes are well-known in the literature.

By hydrolysis of the compounds of the formula I having nitrile, amide or ester groups, there may be prepared compounds with a carboxyl group, which are suitable intermediates for the preparation of other compounds with novel functional groups such as e.g. esters, amides, halides, anhydrides, alcohols or amines.

Oxidation or reduction reactions are a further possibility of the change of substituents in the compounds of the formula I. Most frequently used oxidation agents are peroxides (hydrogen peroxide, m-chloroperbenzoic acid or benzoyl peroxide) or permanganate, chromate or perchlorate ions. Thus e.g. by the oxidation of an alcohol group by pyridinyl dichromate or pyridinyl chlorochromate, an aldehyde group is formed, which group may be converted to a carboxyl group by further oxidation. By oxidation of the compounds of the formula I, wherein $R^1$ has the meaning of alkyl, with lead tetraacetate in acetic acid or with N-bromosuccinimide using a catalytic amount of benzoyl peroxide, a corresponding carbonyl derivative is obtained.

By a selective oxidation of alkylthio group, alkylsulfinyl or alkylsulfonyl groups may be prepared.

By the reduction of the compounds with a nitro group, the preparation of amino compounds is made possible. The reaction is carried out under usual conditions of catalytic hydrogenation or electrochemically. By catalytic hydrogenation using palladium on carbon, alkenyl substituents may be converted to alkyl ones or nitrile group can be converted to aminoalkyl.

Various substituents of the aromatic structure in the compounds of the formula I may be introduced by standard substituion reactions or by usual changes of individual functional groups. Examples of such reactions are aromatic substitutions, alkylations, halogenation, hydroxylation as well as oxidation or reduction of substituents. Reagents and reaction conditions are known from the literature. Thus e.g. by aromatic substitution a nitro group is introduced in the presence of concentrated nitric acid and sulfuric acid. By using acyl halides or alkyl halides, the introduction of an acyl group or an alkyl group is made possible. The reaction is carried out in the presence of Lewis acids such as aluminum- or iron-trichloride in conditions of Friedel-Crafts reaction. By the reduction of the nitro group, an amino group is obtained, which is by the reaction of diazotizing converted to a suitable starting group, which may be replaced with one of the following groups: H, CN, OH, Hal.

In order to prevent undesired interaction in chemical reactions, it is often necessary to protect certain groups such as e.g. hydroxy, amino, thio or carboxy. For this purpose a great number of protecting groups may be used (Green T W, Wuts P G H, Protective Groups in Organic Synthesis, John Wiley and Sons, 1999) and the choice, use and elimination thereof are conventional methods in chemical synthesis.

A convenient protection for amino or alkylamino groups are groups such as e.g. alkanoyl (acetyl), alkoxycarbonyl (methoxycarbonyl, ethoxycarbonyl or tert-butoxycarbonyl); arylmethoxycarbonyl (benzyloxycarbonyl), aroyl (benzoyl) or alkylsilyl (trimethylsilyl or trimethylsilylethoxymethyl) groups. The conditions of removing a protecting group depend upon the choice and the characteristics of this group. Thus e.g. acyl groups such as alkanoyl, alkoxycarbonyl or aroyl may be eliminated by hydrolysis in the presence of a base (sodium hydroxide or potassium hydroxide), tert-butoxycarbonyl or alkylsilyl (trimethylsilyl) may be eliminated by treatment with a suitable acid (hydrochloric, sulfuric, phosphoric or trifluoroacetic acid), whereas arylmethoxycarbonyl group (benzyloxycarbonyl) may be eliminated by hydrogenation using a catalyst such as palladium on carbon.

Salts of the compounds of the formula I may be prepared by generally known processes such as e.g. by reacting the compounds of the formula I with a corresponding base or acid in an appropriate solvent or solvent mixture e.g. ethers (diethylether) or alcohols (ethanol, propanol or isopropanol).

Another object of the present invention concerns the use of the present compounds in the therapy of inflammatory diseases and conditions, especially all diseases and conditions induced by excessive TNF-α and IL-1 secretion.

Inhibitors of production of cytokins or inflammation mediators, which are the object of the present invention, or pharmacologically acceptable salts thereof may be used in production of drugs for the treatment and prophylaxis of any pathological condition or disease induced by excessive unregulated production of cytokins or inflammation mediators, which drugs should contain an effective dose of said inhibitors.

The present invention specifically relates to an effective dose of TNF-α inhibitor, which may be determined by usual methods.

Further, the present invention relates to a pharmaceutical formulation containing an effective non-toxic dosis of the present compounds as well as pharmaceutically acceptable carriers or solvents.

The preparation of pharmaceutical formulations may include blending, granulating, tabletting and dissolving ingredients. Chemical carriers may be solid or liquid. Solid carriers may be lactose, sucrose, talcum, gelatine, agar, pectin, magnesium stearate, fatty acids etc. Liquid carriers may be syrups, oils such as olive oil, sunflower oil or soya bean oil, water etc. Similarly, the carrier may also contain a component for a sustained release of the active component such as e.g. glyceryl monostearate or glyceryl distearate. Various forms of pharmaceutical formulations may be used. Thus, if a solid carrier is used, these forms may be tablets, hard gelatine capsules, powder or granules, which may be administered in capsules per os. The amount of the solid carrier may vary, but it is mainly from 25 mg to 1 g. If a liquid carrier is used, the formulation would be in the form of a syrup, emulsion, soft gelatine capsules, sterile injectable liquids such as ampoules or non-aqueous liquid suspensions.

Compounds according to the present invention may be applied per os, parenterally, locally, intranasally, intrarectally and intravaginally. The parenteral route herein means intravenous, intramuscular and subcutaneous applications. Appropriate formulations of the present compounds may be used in the prophylaxis as well as in the treatment of various diseases and pathological inflammatory conditions induced by an excessive unregulated production of cytokines or inflammation mediators, primarily TNF-α. They comprise rheumatoid arthritis, rheumatoid spondylitis, osteoarthritis and other arthritic pathological conditions and diseases, eczemas, psoriasis and other inflammatory skin conditions such as burns induced by UV radiation (sun rays and similar UV sources), inflammatory eye diseases, Crohn's disease, ulcerative colitis and asthma.

The inhibitory action of the present compounds upon TNF-α and IL-1 secretion was determined by the following in vitro and in vivo experiments:

Determination of TNF-α and IL-1 Secretion in Human Peripheral Blood Mononuclear Cells in vitro Human peripheral blood mononuclear cells (PBMC) were prepared from heparinized whole blood after separating PBMC on Ficoll-Paque™Plus (Amersham-Pharmacia). To determine the TNF-α level, $3.5-5 \times 10^4$ cells were cultivated in a total volume of 200 μl for 18 to 24 hours on microtitre plates with a flat bottom (96 wells, Falcon) in RPMI 1640 medium, into which there were added 10% FBS (Fetal Bovine Serum, Biowhittaker) previously inactivated at 54° C./30 min, 100 units/ml of penicillin, 100 mg/ml of streptomycin and 20 mM HEPES (GIBCO). The cells were incubated at 37° C. in an atmosphere with 5% $CO_2$ and 90% humidity. In a negative control the cells were cultivated only in the medium (NC), whereas in a positive control TNF-α secretion was triggered by adding 1 ng/ml of lipopolysaccharides (LPS, E. coli serotype 0111:B4, SIGMA) (PC). The effect of the tested substances upon TNF-α secretion was investigated after adding them into cultures of cells stimulated by LPS (TS). The TNF-α level in the cell supernatant was determined by ELISA procedure according to the suggestions of the producer (R&D Systems). The test sensitivity was <3 pg/ml TNF-α. The IL-1 level was determined in an assay under the same conditions and with the same number of cells and the same concentration of the stimulus by ELISA procedure (R&D Systems). The percentage of inhibition of TNF-α or IL-1 production was calculated by the equation:

% inhibition=$[1-(TS-NC)/(PC-NC)]*100$.

The IC-50 value was defined as the substance concentration, at which 50% of TNF-α production were inhibited.

Compounds showing IC-50 with 20 μM or lower concentrations are active.

Determination of TNF-α and IL-1 Secretion in Mouse Peritoneal Macrophages in vitro In order to obtain peritoneal macrophages, Balb/C mouse strain males, age 8 to 12 weeks, were injected i.p. with 300 μg of zymosan (SIGMA) dissolved in a phosphate buffer (PBS) in a total volume of 0.1 ml/mouse. After 24 hours the mice were euthanized according to the Laboratory Animal Welfare Act. The peritoneal cavity was washed with a sterile physiological solution (5 ml). The obtained peritoneal macrophages were washed twice with a sterile physiological solution and, after the last centrifugation (350 g/10 min), resuspended in RPMI 1640, into which 10% of FBS portion were added. In order to determine TNF-α secretion, $5 \times 10^4$ cells/well were cultivated in a total volume of 200 μl for 18 to 24 hours on microtitre plates with a flat bottom (96 wells, Falcon) in RPMI 1640 medium, into which 10% FBS (Fetal Bovine Serum, Biowhittaker) inactivated by heat, 100 units/ml of penicillin, 100 mg/ml of streptomycin, 20 mM HEPES and 50 μM 2-mercaptoethanol (all of GIBCO) were added. The cells were incubated at 37° C. in an atmosphere with 5% $CO_2$ and 90% humidity. In a negative control the cells were cultivated only in a medium (NC), whereas in a positive control the TNF-α secretion was triggered by adding 10 ng/ml of lipopolysaccharides (LPS, E. coli serotype 0111:B4, SIGMA) (PC). The effect of the substances upon the TNF-α secretion was investigated after adding them into cultures of cells stimulated with LPS (TS). The TNF-α level in the cell supernatant was determined by ELISA procedure (R&D Systems, Biosource). The IL-1 level was determined in an assay identical to the assay for TNF-α by ELISA procedure (R&D Systems). The percentage of inhibition of TNF-α or IL-1 production was calculated by the equation:

% inhibition=[1−(TS−NC)/(PC−NC)]*100.

The IC-50 value was defined as the substance concentration, at which 50% of TNF-α production were inhibited.

Compounds showing IC-50 with 10 μM or lower concentrations are active.

In vivo Model of LPS-induced Excessive TNF-α or IL-1 Secretion in Mice

TNF-α or IL-1 secretion in mice was induced according to the already disclosed method (Badger A M et al., *J. Pharmac. Env. Therap.*, 1996, 279:1453-1461). Balb/C males, age 8 to 12 weeks, in groups of 6 to 10 animals were used. The animals were treated p.o. either with a solvent only (in negative and in positive controls) or with solutions of substances 30 minutes prior to i.p. treatment with LPS (*E. coli* serotype 0111:B4, Sigma) in a dosis of 25 μg/animal. Two hours later the animals were euthanized by means of i.p. Roumpun (Bayer) and Ketanest (Parke-Davis) injection. A blood sample of each animal was taken into a Vacutainer tube (Becton Dickinson) and the plasma was separated according to the producer's instructions. The TNF-α level in the plasma was determined by ELISA procedure (Biosource, R&D Systems) according to the producer's instructions. The test sensitivity was <3 pg/ml TNF-α. The IL-1 level was determined by ELISA procedure (R&D Systems). The percentage of inhibition of TNF-α or IL-1 production was calculated by the equation:

% inhibition=[1−(TS−NC)/(PC−NC)]*100.

Active are the compounds showing 30% or more inhibition of TNF-α production at a dosis of 10 mg/kg.

Writhing Assay for Analgetic Activity

In this assay pain is induced by the injection of an irritant, most frequently acetic acid, into the peritoneal cavity of mice. Animals react with characteristic writhings, which has given the name of the assay (Collier H O J et al., *Pharmac. Chemother.*, 1968, 32:295-310; Fukawa K et al., *J. Pharmacol. Meth.*, 1980, 4:251-259; Schweizer A et al., *Agents Actions*, 1988, 23:29-31). The assay is convenient for the determination of analgetic activity of compounds. Procedure: male Balb/C mice (Charles River, Italy), age 8 to 12 weeks, were used. A control group received methyl cellulose p.o. 30 minutes prior to i.p. application of acetic acid in a concentration of 0.6%, whereas test groups received standard (acetylsalicylic acid) or test substances in methyl cellulose p.o. 30 minutes prior to i.p. application of 0.6% acetic acid (volume 0.1 ml/10 g). The mice were placed individually under glass funnels and the number of writhings was registered for 20 minutes for each animal. The percentage of writhing inhibition was calculated according to the equation:

% inhibition=(mean value of number of writhings in the control group−number of writhings in the test group)/number of writhings in the control group*100.

Active are the compounds showing such analgetic activity as acetylsalicylic acid or better.

In vivo Model of LPS-induced Shock in Mice

Male Balb/C mice (Charles River, Italy), age 8 to 12 weeks, were used. LPS isolated from *Serratie marcessans* (Sigma, L-6136) was diluted in sterile physiological solution. The first LPS injection was administered intradermally in a dosis of 4 μg/mouse. 18 to 24 hours later, LPS was administered i.v. in a dosis of 200 μg/mouse. A control group received two LPS injections as disclosed above. The test groups received substances p.o. half an hour prior to each LPS application. Survival after 24 hours was observed.

Active are the substances at which the survival at a dosis of 30 mg/kg was 40% or more.

Compounds from Examples 6 and 7 show activity in at least two investigated assays though these results only represent an illustration of biological activity of compounds and should not limit the invention in any way.

PREPARATION PROCESSES WITH EXAMPLES

The present invention is illustrated by the following Examples which are in no way a limitation thereof.

Example 1

8-Oxa-1-thia-benzo[e]naphtho[3,2-h]azulene-2-carboxylic acid ethyl ester (48; Table 1)

Ethyl-2-mercaptoacetate (0.005 mole) and triethyl amine (1.0 ml) were added to a pyridine solution of the compound 41 (0.005 mole in 10 ml) and the mixture was refluxed under stirring for 3 hours. Then pyridine was removed under reduced pressure. Water and ethyl acetate were added to the residue, the layers were separated and the aqueous layer was twice more extracted with ethyl acetate. The organic layer was dried on sodium sulfate and evaporated. There remained a crude product, which was purified by recrystallization or column chromatography to give a pure product in the form of a white solid.

According to the above process, starting from compounds 42-47 there were prepared and isolated:
1,8-dithia-benzo[e]naphtho[3,2-h]azulene-2-carboxylic acid ethyl ester;
3,10-dithia-benzo[e]naphtho[1,2-h]azulene-2-carboxylic acid ethyl ester;
10-oxa-3-thia-benzo[e]naphtho[1,2-h]azulene-2-carboxylic acid ethyl ester;
11-methoxy-8-oxa-1-thia-benzo[e]naphtho[3,2-h]azulene-2-carboxylic acid ethyl ester;
6,7,8,9-tetrahydro-10-oxa-3-thia-benzo[]naphtho[1,2-h]azulene-2-carboxylic acid ethyl ester;
10,11,12,13-tetrahydro-8-oxa-1-thia-benzo[e]naphtho[3,2-h]azulene-2-carboxylic acid ethyl ester (Table 1, compounds 49-54)

Example 2

(8-Oxa-1-thia-benzo[e]naphtho[3,2-h]azulene-2-yl)-methanol (55; Table 1)

An ether solution of ester 48 (1.5 mmole in 20 ml) was added dropwise to a suspension of $LiAlH_4$ in ether (5.0 mmole in 10 ml). The reaction mixture was stirred at room temperature for 2 hours. After the completion of reaction the excess of $LiAlH_4$ was decomposed by addition of ether and water. The obtained precipitate was filtered off and the filtrate was evaporated under reduced pressure. A crude product was purified by recrystallization to obtain a pure product in the form of white crystals.

According to the above process, starting from compounds 49-54 there were prepared and isolated:
(1,8-dithia-benzo[e]naphtho[3,2-h]azulene-2-yl)-methanol;

(3,10-dithia-benzo[e]naphtho[1,2-h]azulene-2-yl)-methanol;

(10-oxa-3-thia-benzo[e]naphtho[1,2-h]azulene-2-yl)-methanol;

(11-methoxy-8-oxa-1-thia-benzo[e]naphtho[3,2-h]azulene-2-yl)-methanol;

(6,7,8,9-tetrahydro-10-oxa-3-thia-benzo[e]naphtho[1,2-h]azulene-2-yl)-methanol;

(10,11,12,13-tetrahydro-8-oxa-1-thia-benzo[e]naphtho[3,2-h]azulene-2-yl)-methanol; (Table 1; compounds 56-61).

catalytic amount of benzyltriethylammonium chloride and a solution of alcohol 55 (0.3 mmole) in toluene (5 ml) were added. The reaction mixture was heated under reflux and vigorous stirring for 4 hours. Then it was cooled to room temperature, diluted with water and extracted with dichloromethane. After purifying by column chromatography, a yellow oily product was isolated.

$^1$H NMR (ppm, CDCl$_3$): 2.31 (s, 6H); 2.60 (t, 2H); 3.68 (t, 2H); 4.78 (s, 2H); 7.18-7.50 (m, 7H); 7.73 (s, 1H); 7.80 (m, 2H); 7.90 (s, 1H); MS (m/z): 402 (MH$^+$).

TABLE 1

Compounds of the structure I wherein Y = Z = H

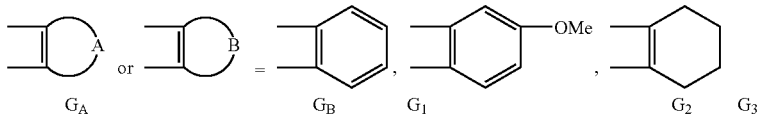

| comp. | X | G$_A$ | G$_B$ | R$^1$ | MS (m/z) | $^1$H NMR (ppm) |
|---|---|---|---|---|---|---|
| 48 | O | | G$_1$ | CO$_2$Et | — | 1.36 (t, 3H); 4.38 (q, 2H); 7.32 (m, 1H); 7.45-7.60 (m, 4H); 7.77 (d, 1H); 7.95 (d, 1H); 7.99 (s, 1H); 8.04 (d, 1H); 8.22 (s, 1H); 8.27 (s, 1H) (DMSO-d$_6$) |
| 49 | S | | G$_1$ | CO$_2$Et | — | 1.43 (t, 3H); 4.42 (q, 2H); 7.30-7.56 (m, 5H); 7.70 (d, 1H); 7.82 (m, 2H); 8.01 (s, 1H); 8.04 (s, 1H); 8.17 (s, 1H)(CDCl$_3$) |
| 50 | S | | G$_1$ | CO$_2$Et | — | 1.34 (t, 3H); 4.20 (q, 2H); 7.10-8.10 (m, 10H); 9.20 (d, 1H)(CDCl$_3$) |
| 51 | O | | G$_1$ | CO$_2$Et | — | 1.43 (t, 3H); 4.42 (q, 2H); 7.21-7.73 (m, 8H); 7.85 (d, 1H); 8.09 (s, 1H); 8.67 (d, 1H)(CDCl$_3$) |
| 52 | O | | G$_2$ | CO$_2$Et | 403 (MH$^+$) | 1.36 (t, 3H); 3.90 (s, 3H); 4.37 (q, 2H); 7.18 (dd, 1H); 7.29-7.36 (m, 2H); 7.46-7.50 (m, 2H); 7.76 (d, 1H); 7.86 (s, 1H); 7.95 (d, 1H); 8.18 (s, 1H), 8.20 (s, 1H)(CDCl$_3$) |
| 53 | O | | G$_3$ | CO$_2$Et | 377 (MH$^+$) | 1.34 (t, 3H); 1.74 (m, 2H); 1.80 (m, 2H); 2.74 (m, 2H); 3.06 (m, 2H); 4.35 (q, 2H); 7.02 (d, 1H); 7.28-7.44 (m, 4H); 7.72 (d, 1H); 8.14 (s, 1H) (DMSO-d$_6$) |
| 54 | O | | G$_3$ | CO$_2$Et | 377 (MH$^+$) | 1.34 (t, 3H); 1.71 (bs, 4H); 2.73 (m, 4H); 4.35 (q, 2H); 7.16 (s, 1H); 7.27-7.31 (m, 2H); 7.37-7.46 (m, 2H); 7.70 (d, 1H); 8.15 (s, 1H)(DMSO-d$_6$) |
| 55 | O | | G$_1$ | CH$_2$OH | — | 4.76 (d, 2H); 5.74 (t, 1H); 7.27-7.62 (m, 7H); 7.92 (m, 1H); 7.93 (s, 1H); 8.00 (m, 1H); 8.05 (s, 1H) (DMSO-d$_6$) |
| 56 | S | | G$_1$ | CH$_2$OH | — | 1.70 (bs, 1H), 4.95 (s, 2H); 7.25-7.51 (m, 6H); 7.70 (d, 1H); 7.81 (m, 2H); 7.98 (s, 1H); 8.16 (s, 1H) (CDCl$_3$) |
| 57 | S | | G$_1$ | CH$_2$OH | — | 1.58 (bs, 1H); 5.00 (s, 2H); 7.20-7.90 (m, 10H); 9.09 (d, 1H)(CDCl$_3$) |
| 58 | O | | G$_1$ | CH$_2$OH | — | 1.69 (bs, 1H); 4.94 (s, 2H); 7.18-7.67 (m, 9H); 7.83 (d, 1H); 8.66 (d, 1H)(CDCl$_3$) |
| 59 | O | | G$_2$ | CH$_2$OH | 361 (MH$^+$) | — |
| 60 | O | | G$_3$ | CH$_2$OH | 334 (M$^+$) | 1.72 (m, 2H); 1.81 (m, 2H); 2.73 (t, 2H); 3.05 (t, 2H); 4.71 (d, 2H); 5.64 (t, 1H); 6.96 (d, 1H); 7.16 (d, 1H); 7.26 (m, 1H); 7.32 (s, 1H); 7.36-7.40 (m, 2H); 7.56 (d, 1H)(DMSO-d$_6$) |
| 61 | O | | G$_3$ | CH$_2$OH | 334 (M$^+$) | 1.71 (bs, 4H); 2.71 (m, 4H); 4.71 (d, 2H); 5.65 (t, 1H); 7.09 (s, 1H); 7.11 (s, 1H); 7.22-7.41 (m, 4H); 7.54 (d, 1H)(DMSO-d$_6$) |

Example 3 a) Dimethyl-[2-(8-oxa-1-thia-benzo[e]naphtho[3,2-h]azulene-2-ylmethoxy)-ethyl]-amine To a solution of 2-dimethylaminoethyl chloride hydrochloride (3.0 mmole) in 50% sodium hydroxide (5 ml), a b) Dimethyl-[3-(8-oxa-1-thia-benzo[e]naphtho[3,2-h]azulene-2-ylmethoxy)-propyl]-amine By the reaction of alcohol 55 (0.2 mmole) and 3-dimethylaminopropyl chloride hydrochloride (2.0 mmole), a yellow oily product was obtained.

¹H NMR (ppm, CDCl₃): 2.01 (m, 2H); 2.50 (s, 6H); 2.75 (t, 2H); 3.68 (t, 2H); 4.75 (s, 2H); 7.18-7.73 (m, 7H); 7.73 (s, 1H); 7.80 (m, 2H); 7.90 (s, 1H); MS (m/z): 416 (MH⁺).

c) 3-(8-Oxa-1-thia-benzo[e]naphtho[3,2-h]azulene-2-ylmethoxy)-propylamine

By the reaction of alcohol 55 (0.3 mmole) and 3-aminopropyl chloride hydrochloride (3.0 mmole), a yellow oily product was obtained.

¹H NMR (ppm, CD₃COCD₃): 1.90 (m, 2H); 2.86 (b, 2H); 3.30 (t, 2H); 3.68 (t, 2H); 4.78 (s, 2H); 7.25-7,65 (m, 7H); 7.89 (s, 1H); 7.90-8.00 (m, 2H); 8.04 (s, 1H); MS (m/z): 388 (MH⁺).

Example 4

Dimethyl-[3-(1,8-dithia-benzo[e]naphtho[3,2-h]azulene-2-ylmethoxy)-propyl]-amine To a solution of 2-dimethylaminopropyl chloride hydrochloride (8.0 mmole) in 50% sodium hydroxide (10 ml), a catalytic amount of benzyltriethylammonium chloride and a solution of alcohol 56 (0.6 mmole) in toluene (10 ml) were added. The reaction mixture was heated under reflux and vigorous stirring for 4 hours. Then it was cooled to room temperature, diluted with water and extracted with dichloromethane. After purifying by column chromatography, a yellow oily product was isolated.

¹H NMR (ppm, CDCl₃): 1.90 (m, 2H); 2.31 (s, 6H); 2.49 (t, 2H); 3.67 (t, 2H); 4.76 (s, 2H); 7.23 (s, 1H); 7.29-7.52 (m, 5H); 7.70 (d, 1H); 7.81 (m, 2H); 7.99 (s, 1H); 8.16 (s, 1H)

Example 5 a) Dimethyl-[2-(3,10-dithia-benzo[e]naphtho[1,2-h]azulene-2-ylmethoxy)-ethyl]-amine To a solution of 2-dimethylaminoethyl chloride hydrochloride (10.0 mmole) in 50% sodium hydroxide (10 ml), a solution of alcohol 57 (0.7 mmole) in toluene (10 ml) was added. The reaction mixture was heated under reflux and vigorous stirring for 4 hours. Then it was cooled to room temperature, diluted with water and extracted with dichloromethane. After purifying by column chromatography, a yellow oily product was isolated.

¹H NMR (ppm, CDCl₃): 2.33 (s, 6H); 2.63 (t, 2H); 3.73 (t, 2H); 4.82 (s, 2H); 7.15-7.80 (m, 10H); 9.02 (d, 1H).

b) Dimethyl-[3-(3,10-dithia-benzo[e]naphtho[1,2-h]azulene-2-ylmethoxy)-propyl]-amine By the reaction of alcohol 57 and 3-dimethylaminopropyl chloride, a yellow oily product was obtained; ¹H NMR (ppm, CDCl₃): 1.87 (m, 2H); 2.27 (s, 6H); 2.45 (t, 2H); 3.68 (t, 2H); 4.78 (s, 2H); 7.20-7.83 (m, 10H); 9.02 (d, 1H); MS (m/z): 432 (MH⁺).

Example 6 a) Dimethyl-[2-(10-oxa-3-thia-benzo[e]naphtho[1,2-h]azulene-2-ylmethoxy)-ethyl]-amine To a solution of 2-dimethylaminoethyl chloride hydrochloride (5.0 mmole) in 50% sodium hydroxide (5 ml), a toluene solution of alcohol 58 (0.5 mmole) was added. The reaction mixture was heated under reflux and vigorous stirring for 3 hours. Then it was cooled to room temperature, diluted with water and extracted with dichloromethane. After purifying by column chromatography, a yellow oily product was isolated.

¹H NMR (ppm, CDCl₃): 2.36 (s, 6H); 2.65 (t, 2H); 3.72 (t, 2H); 4.79 (s, 2H); 7.18-7.67 (m, 9H); 7.83 (d, 1H); 8.66 (d, 1H); MS (m/z): 402 (MH⁺).

b) Dimethyl-[3-(10-oxa-3-thia-benzo[e]naphtho[1,2-h]azulene-2-ylmethoxy)-propyl]-amine By the reaction of alcohol 58 and 3-dimethylaminopropyl chloride hydrochloride, a yellow oily product was obtained.

¹H NMR (ppm, CDCl₃): 1.91 (m, 2H); 2.35 (s, 6H); 2.55 (t, 2H); 3.65 (t, 2H); 4.75 (s, 2H); 7.20-7.67 (m, 9H); 7.83 (d, 1H); 8.66 (d, 1H); MS (m/z): 416 (MH⁺).

Example 7

Dimethyl-[3-(11-methoxy-8-oxa-1-thia-benzo[e]naphtho[3,2-h]azulene-2-ylmethoxy)-propyl]-amine To a solution of 3-dimethylaminopropyl chloride hydrochloride (3.0 mmole) in 50% sodium hydroxide (5 ml), a catalytic amount of benzyltriethylammonium chloride and a solution of alcohol 59 (0.3 mmole) in toluene (5 ml) were added. The reaction mixture was heated under reflux and vigorous stirring for 6 hours. Then it was cooled to room temperature, diluted with water and extracted with dichloromethane. After purifying by column chromatography, a yellow product was isolated, which crystallized upon standing.

¹H NMR (ppm, CDCl₃): 1.86 (p, 2H); 2.25 (s, 6H); 2.41 (t, 2H); 3.64 (t, 2H); 3.92 (s, 3H); 4.74 (s, 2H); 7.07-7.49 (m, 7H); 7.63 (s, 1H); 7.71 (d, 1H); 7.83 (s, 1H); MS (m/z): 446 (MH⁺).

Example 8 a) Dimethyl-[2-(6,7,8,9-tetrahydro-10-oxa-3-thia-benzo[e]naphtho[1,2-h]azulene-2-ylmethoxy)-ethyl]-amine To a solution of 2-dimethylaminoethyl chloride hydrochloride (6.0 mmole) in 50% sodium hydroxide (10 ml), a solution of alcohol 60 (0.6 mmole) in toluene (10 ml) was added. The reaction mixture was heated under reflux and vigorous stirring for 3 hours. Then it was cooled to room temperature, diluted with water and extracted with dichloromethane. After purifying by column chromatography, a yellow oily product was isolated.

¹H NMR (ppm, CDCl₃): 1.79 (m, 2H); 1.86 (m, 2H); 2.43 (s, 6H); 2.73 (m, 2H); 2.77 (t, 2H); 3.12 (t, 2H); 3.75 (t, 2H); 4.75 (s, 2H); 6.90 (d, 1H); 7.14-7.35 (m, 5H); 7.45 (d, 1H); MS (m/z): 406 (MH⁺).

b) Dimethyl-[3-(6,7,8,9-tetrahydro-10-oxa-3-thia-benzo[e]naphtho[1,2-h]azulene-2-ylmethoxy)-propyl]-amine By the reaction of alcohol 60 and 3-dimethylaminopropyl chloride hydrochloride, a yellow oily product was obtained.

¹H NMR (ppm, CDCl₃): 1.80 (m, 2H); 1.88 (m, 2H); 2.02 (m, 2H); 2.51 (s, 6H); 2.75 (m, 2H); 2.79 (t, 2H); 3.14 (t, 2H); 3.67 (t, 2H); 4.73 (s, 2H); 6.89 (d, 1H); 7.15-7.36 (m, 5H); 7.45 (d, 1H); MS (m/z): 420 (MH⁺).

c) 3-(6,7,8,9-Tetrahydro-10-oxa-3-thia-benzo[e]naphtho[1,2-h]azulene-2-ylmethoxy)-propylamine By the reaction of alcohol 60 and 3-aminopropyl chloride hydrochloride, a yellowish oily product was obtained.
$^1$H NMR (ppm, CDCl$_3$): 1.41 (s, 2H); 1.75-1.87 (m, 6H); 2.77 (t, 2H); 2.85 (t, 2H); 3.12 (t, 2H); 3.64 (t, 2H); 4.71 (s, 2H); 6.89 (d, 1H); 7.14-7.36 (m, 5H); 7.45 (d, 1H); MS (m/z): 414 (M+Na$^+$).

Example 9

Methyl-[3-(6,7,8,9-tetrahydro-10-oxa-3-thia-benzo[e]naphtho[1,2-h]azulene-2-ylmethoxy)-propyl]-amine To a methanolic solution of dimethyl-[3-(6,7,8,9-tetrahydro-10-oxa-3-thia-benzo[e]naphtho[1,2-h]azulene-2-ylmethoxy)-propyl]-amine prepared as in Example 8b (1.0 mmole in 30 ml), sodium acetate trihydrate (5.4 mmole) and iodine (1.13 mmole) were added. The reaction mixture was illuminated with a 500 W lamp and stirred at ambient temperature for 5 hours. After the completion of the reaction, a 10% aqueous sodium thiosulfate solution was added to the reaction mixture. The solvent was evaporated under reduced pressure and the residue was extracted with ethyl acetate. A crude product was purified by column chromatography to obtain a pure product in the form of a yellow oil.
$^1$H NMR (ppm, CDCl$_3$): 1.76-1.91 (m, 4H); 2.00 (m, 2H); 2.59 (s, 3H); 2.77 (m, 2H); 2.96 (t, 2H); 3.12 (t, 2H); 3.70 (t, 2H); 4.4-4.7 (b, 1H); 4.74 (s, 2H); 6.89 (d, 1H); 7.15-7.36 (m, 5H); 7.45 (d, 1H); MS (m/z): 406 (MH$^+$).

Example 10 a) Dimethyl-[2-(10,12,13-tetrahydro-8-oxa-1-thia-benzo[e]naphtho[3,2-h]azulene-2-ylmethoxy)-ethyl]-amine To a solution of 2-dimethylaminoethyl chloride hydrochloride (6.0 mmole) in 50% sodium hydroxide (10 ml), a solution of alcohol 61 (0.6 mmole) in toluene (10 ml) was added. The reaction mixture was heated under reflux and vigorous stirring for 3 hours. Then it was cooled to room temperature, diluted with water and extracted with dichloromethane. After purifying by column chromatography, a yellow oily product was isolated.
$^1$H NMR (ppm, CDCl$_3$): 1.77 (m, 4H); 2.38 (s, 6H); 2.67 (m, 2H); 2.75 (m, 4H); 3.71 (t, 2H); 4.75 (s, 2H); 7.01 (s, 1H); 7.12 (s, 1H); 7.14-7.45 (m, 5H); MS (m/z): 406 (MH$^+$).

b) Dimethyl-[3-(10,11,12,13-tetrahydro-8-oxa-1-thia-benzo[e]naphtho[3,2-h]azulene-2-ylmethoxy)-propyl]-amine By the reaction of alcohol 61 and 3-dimethylaminopropyl chloride hydrochloride, a yellow oily product was obtained.
$^1$H NMR (ppm, CDCl$_3$): 1.78 (m, 4H); 1.99 (m, 2H); 2.49 (s, 6H); 2.70-2.80 (m, 6H); 3.65 (t, 2H); 4.71 (s, 2H); 7.01 (s, 1H); 7.12 (s, 1H); 7.14-7.45 (m, 5H); MS (m/z): 420 (MH$^+$).

c) 4-[2-(10,11,12,13-Tetrahydro-8-oxa-1-thia-benzo[e]naphtho[3,2-h]azulene-2-ylmethoxy)-ethyl]-morpholine By the reaction of alcohol 61 and 4-(2-chloroethyl)morpholine hydrochloride, a yellow oily product was obtained.
$^1$H NMR (ppm, CDCl$_3$): 1.77 (m, 4H); 2.53 (b, 4H); 2.66 (m, 2H); 2.75 (m, 4H); 3.70-3.75 (m, 6H); 4.75 (s, 2H); 7.01 (s, 1H); 7.11 (s, 1H); 7.14-7.44 (m, 5H); MS (m/z): 448 (MH$^+$).

d) 1-[2-(10,11,12,13-Tetrahydro-8-oxa-1-thia-benzo[e]naphtho[3,2-h]azulene-2-ylmethoxy)-ethyl]-piperidine By the reaction of alcohol 61 and 1-(2-chloroethyl)piperidine hydrochloride, a yellow oily product was obtained.
$^1$H NMR (ppm, CDCl$_3$): 1.45 (m, 2H); 1.65 (m, 4H); 1.77 (m, 4H); 2.52 (m, 4H); 2.66 (m, 2H); 2.75 (m, 4H); 3.73 (t, 2H); 4.74 (s, 2H); 7.01 (s, 1H); 7.12 (s, 1H); 7.14-7.44 (m, 5H); MS (m/z): 446 (MH$^+$).

e) 1-[2-(10,11,12,13-Tetrahydro-8-oxa-1-thia-benzo[e]naphtho[3,2-h]azulene-2-ylmethoxy)-ethyl]-pyrrolidine By the reaction of alcohol 61 and 1-(2-chloroethyl)pyrrolidine hydrochloride, a yellow oily product was obtained.
$^1$H NMR (ppm, CDCl$_3$): 1.78 (m, 4H); 1.92 (b, 4H); 2.74-2.94 (m, 10H); 3.84 (b, 2H); 4.76 (s, 2H); 7.01 (s, 1H); 7.12 (s, 1H); 7.15-7.45 (m, 5H); MS (m/z): 432 (MH$^+$).

f) Dimethyl-[2-(10,11,12,13-tetrahydro-8-oxa-1-thia-benzo[e]naphtho[3,2-h]azulene-2-ylmethoxy)-propyl]-amine Dimethyl-[1-methyl-(10,11,12,13-tetrahydro-8-oxa-1-thia-benzo[e]naphtho[3,2-h]azulene-2-ylmethoxy)-ethyl]-amine By the reaction of alcohol 61 and 1-dimethylamino-2-propyl chloride hydrochloride, two products were obtained, which were separated and purified by column chromatography to give yellow oily substances, namely:

dimethyl-[2-(10,11,12,13-tetrahydro-8-oxa-1-thia-benzo[e]naphtho[3,2-h]azulene-2-ylmethoxy)-propyl]-amine $^1$H NMR (ppm, CDCl$_3$): 1.25 (d, 3H); 1.77 (m, 4H); 2.36 (s, 6H); 2.40 (m, 1H); 2.60 (m, 1H); 2.75 (m, 4H); 3.90 (b, 1H); 4.80 (m, 2H); 7.00 (s, 1H); 7.12 (s, 1H); 7.14-7.45 (m, 5H); MS (m/z): 420 (MH$^+$), and dimethyl-[1-methyl-(10,11,12,13-tetrahydro-8-oxa-1-thia-benzo[e]naphtho[3,2-h]azulene-2-ylmethoxy)-ethyl]-amine $^1$H NMR (ppm, CDCl$_3$): 1.04 (d, 3H); 1.77 (m, 4H); 2.33 (s, 6H); 2.75 (m, 4H); 2.85 (m, 1H); 3.45 (m, 1H); 3.59 (m, 1H); 4.74 (s, 2H); 7.01 (s, 1H); 7.12 (s, 1H); 7.14-7.44 (m, 5H); MS (m/z): 420 (MH$^+$).

Preparation of Starting Substances

Process A

1-[2-(Naphthalene-2-yloxy)-phenyl]-ethanone (1; Table 2)

A mixture of 2-naphthol (0.035 mole), 2-chloroacetophenone (0.026 mole), potassium carbonate (0.040 mole) and CuCl (100 mg) in isoamyl alcohol (3 ml) was refluxed overnight. Then the reaction mixture was filtered and the precipitate was washed a few times with ethyl acetate and then the filtrate was washed with a 10% aqueous sodium hydroxide solution and water. The solvent was removed by evaporation under reduced pressure and the residue was distilled under high vacuum to give a pure product in the form of a light yellow liquid.

Process B

1-Morpholine-4-yl-2-[2-(naphthalene-2-yloxy)-phenyl]-ethanethione (2; Table 2)

A mixture of the compound 1 (0.058 mole), morpholine (0.08 mole) and sulfur (0.087 mole) was refluxed for about 3 hours. After the completion of the reaction the mixture was poured into hot ethanol, wherefrom the product was precipitated by cooling.

Process C1

2-(Naphthalene-2-ylsulfanyl)-benzoic acid (3; Table 2)

2-Naphthalenethiol (0.06 mole), 2-iodobenzoic acid (0.60 mole) and Cu powder (1 g) were added to an aqueous potassium hydroxide solution (0.21 mole in 110 ml). The reaction mixture was refluxed for 8 hours and then filtered. Concentrated HCl was added drop by drop to the filtrate up to an acidic reaction. The separated white crystals were sucked off, washed a few times with water and dried.

According to the same process, starting from 2-iodobenzoic acid and 1-naphthalenethiol, also 2-(naphthalene-1-ylsulfanyl)-benzoic acid (Table 2; compound 4) was obtained.

Process C2

2-(Naphthalene-1-yloxy)-benzoic acid (5; Table 2)

A mixture of 1-naphthol (0.03 mole), 2-iodobenzoic acid (0.03 mole), potassium carbonate (0.045 mole) and Cu powder (150 mg) in nitrobenzene or xylene (10 ml) was heated at 140° C. for about 1 hour. After the completion of the reaction water (100 ml) was added to the cooled reaction mixture, the organic layer was separated and concentrated HCl was added to the aqueous layer drop by drop up to an acidic reaction. The separated product was extracted with ethyl acetate.

According to the same procedure, starting from 2-iodobenzoic acid and
7-methoxy-2-naphthol;
5,6,7,8-tetrahydro-1-naphthol;
5,6,7,8-tetrahydro-2-naphthol;

there were obtained the following compounds:
2-(7-methoxy-naphthalene-2-yloxy)-benzoic acid;
2-(5,6,7,8-tetrahydro-naphthalene-1-yloxy)-benzoic acid;
2-(5,6,7,8-tetrahydro-naphthalene-2-yloxy)-benzoic acid (Table 2; compounds 6-8)

Process D

[2-(Naphthalene-2-ylsulfanyl)-phenyl]-methanol (9; Table 2)

To a suspension of LiALH$_4$ in diethyl ether (0.1 mole in 100 ml), acid 3 (0.06 mole) was added step by step. After 2 hours of stirring the reaction mixture at room temperature, the excess of LiAlH$_4$ was decomposed by adding ether and water. The obtained precipitate was filtered and the filtrate was evaporated under reduced pressure to give a crude product, which was purified by column chromatography.

According to the same procedure, starting from compounds 4-8 the following compounds were obtained:
[2-(naphthalene-1-ylsulfanyl)-phenyl]-methanol;
[2-(naphthalene-1-yloxy)-phenyl]-methanol;
[2-(7-methoxy-naphthalene-2-yloxy)-phenyl]-methanol;
[2-(5,6,7,8-tetrahydro-naphthalene-1-yloxy)-phenyl]-methanol;
[2-(5,6,7,8-tetrahydro-naphthalene-2-yloxy)-phenyl]-methanol (Table 2; compounds 10-14)

Process E 2-(2-Bromomethyl-phenylsulfanyl)-naphthalene (15; Table 2)

To a dichloromethane solution of alcohol 9 (0.057 mole in 200 ml) cooled to 0° C., PBr$_3$ (0.019 mole) was added stepwise drop by drop and the mixture was stirred at the same temperature for about 30 minutes. After the completion of the reaction the mixture was poured to cool water (100 ml), the organic layer was separated and the aqueous layer was extracted twice with dichloromethane. The dichloromethane layer was shaken once with a saturated sodium hydrogen carbonate solution, dried on Na$_2$SO$_4$ and evaporated under reduced pressure to leave a crude product, which was purified by column chromatography.

According to the same procedure, starting from the compounds 10-14 the following compounds were obtained:
1-(2-bromomethyl-phenylsulfanyl)-naphthalene;
1-(2-bromomethyl-phenoxy)-naphthalene;
2-(2-bromomethyl-phenoxy)-7-methoxy-naphthalene;
5-(2-bromomethyl-phenoxy)-1,2,3,4-tetrahydro-naphthalene;
6-(2-bromomethyl-phenoxy)-1,2,3,4-tetrahydro-naphthalene (Table 2; compounds 16-20)

Process F

[2-(Naphthalene-2-ylsulfanyl)-phenyl]-acetonitrile (21; Table 2)

To an ethanolic solution of bromide 15 (0.05 mole in 60 ml) NaCN (0.063 mole) was added and the reaction mixture was refluxed for 3 hours. After the completion of the reaction ethanol was eliminated under reduced pressure and water (80 ml) and ethyl acetate (80ml) were added to the residue. The layers were separated and the aqueous layer was extracted two more times with ethyl acetate. The combined organic layers were washed with water, dried on Na$_2$SO$_4$ and evaporated under reduced pressure to leave a crude product, which was purified by column chromatography.

According to the same procedure, starting from compounds 16-20 the following compounds were obtained:
[2-(naphthalene-1-ylsulfanyl)-phenyl]-acetonitrile;
[2-(naphthalene-1-yloxy)-phenyl]-acetonitrile;
[2-(7-methoxy-naphthalene-2-yloxy)-phenyl]-acetonitrile;
[2-(5,6,7,8-tetrahydro-naphthalene-1-yloxy)-phenyl]-acetonitrile;
[2-(5,6,7,8-tetrahydro-naphthalene-2-yloxy)-phenyl]-acetonitrile (Table 2; compounds 22-26)

Process G

[2-(Naphthalene-2-yloxy)-phenyl]acetic acid (27; Table 2)

A mixture of 2 (0.04 mole), acetic acid (10 ml) and 50% sulfuric acid (4.5 ml) was stirred under reflux for about 5 hours. After the completion of the reaction the reaction mixture was poured into water (10 ml). The separated crystals were sucked off, dissolved in a 10% aqueous NaOH solution and the solution was extracted twice with dichloromethane. The aqueous layer was acidified with concentrated HCl up to an acidic reaction. The separated crystals were filtered and dried.

Process H

[2-(Naphthalene-2-ylsulfanyl)-phenyl]acetic acid (28; Table 2)

An aqueous KOH solution (0.15 mole in 15 ml) was added to an ethanolic solution of nitrile 21 (0.045 mole in 60 ml). The reaction mixture was stirred under reflux for about 10 hours and then ethanol was evaporated under reduced pressure. The residue was diluted with water and shaken once with ethyl acetate. The aqueous layer was acidified to an acidic reaction in order to separate the product.

According to the same procedure, starting from the compounds 22-26 the following compounds were obtained:

[2-(naphthalene-1-ylsulfanyl)-phenyl]acetic acid;
[2-(naphthalene-1-yloxy)-phenyl]acetic acid;
[2-(7-methoxy-naphthalene-2-yloxy)-phenyl]acetic acid;
[2-(5,6,7,8-tetrahydro-naphthalene-1-yloxy)-phenyl]acetic acid;
[2-(5,6,7,8-tetrahydro-naphthalene-2-yloxy)-phenyl]acetic acid (Table 2; compounds 29-33)

TABLE 2

Compounds of the structure VIII wherein Y = Z = H

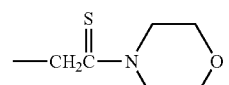

| comp. | X | $G_A$ $G_B$ | $R^5$ | MS (m/z) | $^1$H NMR (ppm) |
|---|---|---|---|---|---|
| 1 | O | $G_1$ | COMe | 263 (MH$^+$) | 2.68 (s, 3H); 6.96-7.97 (m, 11H)(CDCl$_3$) |
| 2 | O | $G_1$ | —CH$_2$C(=S)—N(morpholine) | 364 (MH$^+$) | — |
| 3 | S | $G_1$ | CO$_2$H | — | 6.77-8.23 (m, 11H); 13.50 (b, 1H)(DMSO-d$_6$) |
| 4 | S | $G_1$ | CO$_2$H | — | 4.10 (b, 1H); 6.48 (m, 1H); 7.11 (m, 2H); 7.53 (m, 3H); 7.90-8.32 (m, 5H)(CDCl$_3$) |
| 5 | O | $G_1$ | CO$_2$H | 265 (MH$^+$) | 6.77-8.20 (m, 11H); 12.98 (b, 1H)(DMSO-d$_6$) |
| 6 | O | $G_2$ | CO$_2$H | — | 3.82 (s, 3H); 6.88-8.14 (m, 10H); 12.93 (bs, 1H)(DMSO-d$_6$) |
| 7 | O | $G_3$ | CO$_2$H | — | 1.72 (bs, 4H); 2.61 (bs, 2H); 2.75 (bs, 2H); 6.52 (d, 1H); 6.81-6.88 (m, 2H); 7.06 (t, 1H); 7.20 (m, 1H); 7.49 (t, 1H); 7.79 (m, 1H); 12.83 (bs, 1H)(DMSO-d$_6$) |
| 8 | O | $G_3$ | CO$_2$H | — | 1.71 (m, 4H); 2.66 (bs, 4H); 6.62-7.88 (m, 7H); 12.5-13.0 (b, 1H)(DMSO-d$_6$) |
| 9 | S | $G_1$ | CH$_2$OH | — | 1.92 (bs, 1H); 4.86 (s, 2H); 7.28-7.90 (m, 11H)(CDCl$_3$) |
| 10 | S | $G_1$ | CH$_2$OH | — | 1.79 (bs, 1H); 4.87 (s, 2H); 7.05-7.55 (m, 8H); 7.79-7.90 (m, 2H); 8.31 (m, 1H)(CDCl$_3$) |
| 11 | O | $G_1$ | CH$_2$OH | 250 (M$^+$) | 4.61 (d, 2H); 5.22 (t, 1H); 6.78-8.18 (m, 11H)(DMSO-d$_6$) |
| 12 | O | $G_2$ | CH$_2$OH | — | 3.81 (s, 3H); 4.52 (d, 2H); 5.18 (t, 1H); 6.95-7.86 (m, 10H)(DMSO-d$_6$) |
| 13 | O | $G_3$ | CH$_2$OH | — | 1.71 (bs, 4H); 2.59 (bs, 2H); 2.75 (bs, 2H); 4.56 (d, 2H); 5.16 (t, 1H); 6.51-7.60 (m, 7H)(DMSO-d$_6$) |
| 14 | O | $G_3$ | CH$_2$OH | — | 1.71 (m, 4H); 2.66 (m, 4H); 4.52 (d, 2H); 5.14 (t, 1H); 6.60-6.67 (m, 2H); 6.79 (d, 1H); 7.02 (d, 1H); 7.12-7.26 (m, 2H); 7.52 (m, 1H)(DMSO-d$_6$) |
| 15 | S | $G_1$ | CH$_2$Br | — | 4.80 (s, 2H); 7.24-7.87 (m, 11H)(CDCl$_3$) |
| 16 | S | $G_1$ | CH$_2$Br | — | 4.81 (s, 2H); 6.89-7.21 (m, 3H); 7.40-7.61 (m, 5H); 7.86-7.91 (m, 2H); 8.35 (m, 1H)(CDCl$_3$) |
| 17 | O | $G_1$ | CH$_2$Br | 312;314 (M$^+$) | 4.69 (s, 2H); 6.73-8.27 (m, 11H)(CDCl$_3$) |
| 18 | O | $G_2$ | CH$_2$Br | 342;344 (M$^+$) | 3.83 (s, 3H); 4.73 (s, 2H); 6.93-7.90 (m, 10H)(DMSO-d$_6$) |
| 19 | O | $G_3$ | CH$_2$Br | 316;318 (M$^+$) | 1.71 (bs, 4H); 2.61 (bs, 2H); 2.76 (bs, 2H); 4.74 (d, 2H); 6.58 (d, 1H); 6.68 (d, 1H); 6.93 (d, 1H); 7.02-7.36 (m, 3H); 7.53 (d, 1H)(DMSO-d$_6$) |
| 20 | O | $G_3$ | CH$_2$Br | 316;318 (M$^+$) | 1.72 (m, 4H); 2.69 (bs, 4H); 4.70 (s, 2H); 6.72-6.80 (m, 3H); 7.06-7.12 (m, 2H); 7.30 (m, 1H); 7.53 (d, 1H)(DMSO-d$_6$) |

TABLE 2-continued

Compounds of the structure VIII wherein Y = Z = H

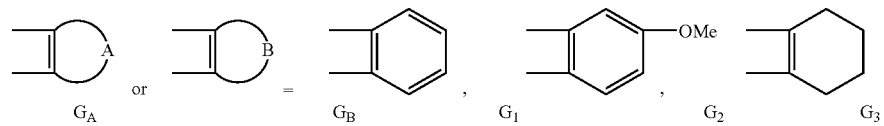

| comp. | X | $G_A$ | $G_B$ | $R^5$ | MS (m/z) | $^1$H NMR (ppm) |
|---|---|---|---|---|---|---|
| 21 | S | | $G_1$ | $CH_2CN$ | 276 (MH$^+$) | — |
| 22 | S | $G_1$ | | $CH_2CN$ | 276 (MH$^+$) | — |
| 23 | O | $G_1$ | | $CH_2CN$ | 259 (M$^+$) | 3.87 (s, 2H); 6.73-8.28 (m, 11H)(CDCl$_3$) |
| 24 | O | | $G_2$ | $CH_2CN$ | 290 (MH+) | 3.84 (s, 3H); 4.02 (s, 2H); 6.96-7.91 (m, 10H) (DMSO-d$_6$) |
| 25 | O | $G_3$ | | $CH_2CN$ | — | 1.71 (bs, 4H); 2.59 (bs, 2H); 2.77 (bs, 2H); 4.00 (s, 2H); 6.54-6.70 (m, 2H); 6.95 (d, 1H); 7.03-7.31 (m, 3H); 7.47 (d, 1H)(DMSO-d$_6$) |
| 26 | O | | $G_3$ | $CH_2CN$ | 264 (MH$^+$) | 1.72 (m, 4H); 2.67 (m, 4H); 3.96 (s, 2H); 6.61-7.49 (m, 7H)(DMSO-d$_6$) |
| 27 | O | $G_1$ | | $CH_2CO_2H$ | — | 3.63 (s, 2H); 6.92-7.97 (m, 11H); 12.25 (bs, 1H)(DMSO-d$_6$) |
| 28 | S | | $G_1$ | $CH_2CO_2H$ | — | 3.91 (s, 2H); 7.28-7.82 (m, 11H)(DMSO-d$_6$) |
| 29 | S | $G_1$ | | $CH_2CO_2H$ | — | 3.90 (s, 2H); 6.97 (d, 1H); 7.18-7.69 (m, 7H); 8.01-8.10 (m, 2H); 8.24 (m, 1H); 12.60 (b, 1H) (DMSO-d$_6$) |
| 30 | O | $G_1$ | | $CH_2CO_2H$ | — | 3.68 (s, 2H); 6.71-8.13 (m, 11H); 12.32 (bs, 1H) (DMSO-d$_6$) |
| 31 | O | | $G_2$ | $CH_2CO_2H$ | 309 (MH$^+$) | 3.60 (s, 2H); 3.82 (s, 3H); 6.93-7.42 (m, 8H); 7.78-7.86 (m, 2H); 12.14 (bs, 1H)(DMSO-d$_6$) |
| 32 | O | $F_3$ | | $CH_2CO_2H$ | — | 1.71 (bs, 4H); 2.58 (bs, 2H); 2.75 (bs, 2H); 3.59 (s, 2H); 6.55-6.63 (m, 2H); 6.88 (d, 1H); 7.01-7.34 (m, 4H)(DMSO-d$_6$) |
| 33 | O | | $G_3$ | $CH_2CO_2H$ | — | 1.71 (m, 4H); 2.66 (m, 4H); 3.58 (s, 2H); 6.63-7.35 (m, 7H); 12.17 (bs, 1H)(DMSO-d$_6$) |

Process I 13H-5-Oxa-benzo[4,5]cyclohepta[1,2-b]naphthalene-12-one (34; Table 3)

A mixture of an acid 27 and polyphosphoric acid (PPA; 3.0 g in 30 g) was vigorously stirred at 100° C. for about 2 hours. The reaction mixture was then poured into water and extracted three times with dichloromethane. The dichloromethane layer was dried on Na$_2$SO$_4$ and evaporated under reduced pressure to leave a crude product, which may be purified by column chromotography or recrystallization.

According to the same procedure, starting from the compounds 28-33 following compounds were obtained:

13H-5-thia-benzo[4,5]cyclohepta[1,2-b] naphthalene-12-one;
8H-13-thia-benzo[5,6]cyclohepta[1,2-b]naphthalene-7-one;
8H-13-oxa-benzo[5,6]cyclohepta[1,2-a]naphthalene-7-one;
8-methoxy-13H-5-oxa-benzo[4,5]cyclohepta[1,2-b]naphthalene-12-one;
1,2,3,4-tetrahydro-8H-13-oxa-benzo[5,6]cyclohepta[1,2-a] naphthalene-7-one;
7,8,9,10-tetrahydro-13H-5-oxa-benzo[4,5]cyclohepta[1,2-b]naphthalene-12-one (Table 3; compounds 35-40)

TABLE 3

Compounds of the formula VI wherein Y = Z = H

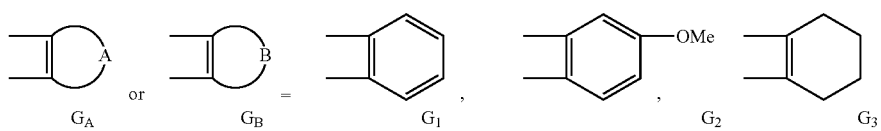

| comp. | X | $G_A$ | $G_B$ | MS (m/z) | $^1$H NMR (ppm) |
|---|---|---|---|---|---|
| 34 | O | | $G_1$ | 261 (MH$^+$) | 4.22 (s, 2H); 7.12-7.99 (m, 9H); 8.66 (s, 1H)(CDCl$_3$) |
| 35 | S | | $G_1$ | — | 4.55 (s, 2H); 7.19-7.93 (m, 8H); 8.11 (s, 1H); 8.78 (s, 1H)(CDCl$_3$) |
| 36 | S | $G_1$ | | — | 4.55 (s, 2H); 7.06-8.32 (m, 9H); 8.91 (s, 1H)(CDCl$_3$) |

TABLE 3-continued

Compounds of the formula VI wherein Y = Z = H $G_A$ or $G_B$ = $G_1$, $G_2$ (with OMe), $G_3$

| comp. | X | $G_A$ | $G_B$ | MS (m/z) | $^1$H NMR (ppm) |
|---|---|---|---|---|---|
| 37 | O | $G_1$ | | 261 (MH$^+$) | 4.20 (s, 2H); 7.15-7.84 (m, 8H); 8.04 (d, 1H); 8.77 (m, 1H)(CDCl$_3$) |
| 38 | O | | $G_2$ | 291 (MH$^+$) | 3.94 (s, 3H); 4.19 (s, 2H); 7.07-7.35 (m, 6H); 7.66 (s, 1H); 7.79 (d, 1H); 8.57 (s, 1H)(DMSO-d$_6$) |
| 39 | O | $G_3$ | | 265 (MH$^+$) | 1.70-1.90 (m, 4H); 2.78 (m, 2H); 3.04 (m, 2H); 4.08 (s, 2H); 6.97 (d, 1H), 7.22-7.44 (m, 4H); 7.66 (d, 1H) (DMSO-d$_6$) |
| 40 | O | | $G_3$ | 265 (MH$^+$) | 1.72 (m, 4H); 2.71 (bs, 2H); 2.80 (bs, 2H); 4.08 (s, 2H); 7.18 (s, 1H); 7.20-7.43 (m, 4H); 7.61 (s, 1H) (DMSO-d$_6$) |

Process J

12-Chloro-5-oxa-benzo[4,5]cyclohepta[1,2-b]naphthalene-13-carbaldehyde (41; Table 4)

A trichloroethene solution of the compound 34 (0.008 mole in 5 ml) was added drop by drop to a solution of Vilsmeier-Hack reagent in trichloroethene (0.01 mole in 5 ml). The reaction mixture was then refluxed for about 6 hours, whereupon it was cooled and 20 ml of a 50% aqueous sodium acetate solution were added stepwise drop by drop thereto. The layers were separated and the aqueous layer was extracted three times with dichloromethane. The dichloromethane layers dried on Na$_2$SO$_4$ were evaporated under reduced pressure to leave a crude product, which may be purified by recrystallization or column chromatography.

According to the same procedure, starting from the compounds 35-40 the following compounds were obtained:

12-chloro-5-thia-benzo[4,5]cyclohepta[1,2-b]naphthalene-13-carbaldehyde;

7-chloro-13-thia-benzo[5,6]cyclohepta[1,2-a]naphthalene-8-carbaldehyde;

7-chloro-13-oxa-benzo[5,6]cyclohepta[1,2-a]naphthalene-8-carbaldehyde;

12-chloro-8-methoxy-5-oxa-benzo[4,5]cyclohepta[1,2-b] naphthalene-13-carbaldehyde;

7-chloro-1,2,3,4-tetrahydro-13-oxa-benzo[5,6]cyclohepta [1,2-a]naphthalene-8-carbaldehyde;

12-chloro-7,8,9,10-tetrahydro-5-oxa-benzo[4,5]cyclohepta [1,2-b]naphthalene-13-carbaldehye; (Table 4; compounds 42-47)

TABLE 4

Compounds of the formula III wherein Y = Z = H $G_A$ or $G_B$ = $G_1$, $G_2$ (with OMe), $G_3$

| comp | X | $G_A$ | $G_B$ | MS (m/z) | $^1$H NMR (ppm) |
|---|---|---|---|---|---|
| 41 | O | | $G_1$ | — | 7.19-7.94 (m, 9H); 8.38 (s, 1H); 10.73 (s, 1H)(CDCl$_3$) |
| 42 | S | | $G_1$ | — | 7.18-7.91 (m, 8H); 8.07 (s, 1H); 8.32 (s, 1H); 10.75 (s, 1H) (CDCl$_3$) |
| 43 | S | $G_1$ | | — | 7.03-8.25 (m, 9H); 8.94 (m, 1H); 10.79 (s, 1H)(CDCl$_3$) |
| 44 | O | $G_1$ | | 307 (MH$^+$) | 7.18-7.87 (m, 9H); 8.65 (d, 1H); 10.73 (s, 1H)(CDCl$_3$) |
| 45 | O | | $G_2$ | 337 (MH$^+$) | 3.91 (s, 3H); 7.20-7.49 (m, 6H); 7.82 (s, 1H); 8.04 (d, 1H); 8.48 (s, 1H); 10.73 (s, 1H)(DMSO-d$_6$) |
| 46 | O | | $G_3$ | 311 (MH$^+$) | 1.65-1.85 (m, 4H); 2.76 (m, 2H); 3.02 (bs, 2H); 7.11 (d, 1H); 7.23-7.47 (m, 4H); 7.56 (d, 1H); 10.51 (s, 1H) (DMSO-d$_6$) |
| 47 | O | $G_3$ | | 311 (MH$^+$) | 1.71 (m, 4H); 2.70-2.77 (m, 4H); 7.14 (s, 1H); 7.21-7.47 (m, 4H); 7.52 (s, 1H); 10.52 (s, 1H)(DMSO-d$_6$) |

The invention claimed is:

1. A compound of the formula I

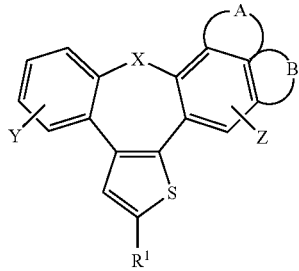

wherein

X is selected from the group consisting of $CH_2$, O, S, S(=O), S(=O)$_2$, and $NR^a$, wherein $R^a$ is hydrogen or a protecting group;

Y and Z are each independently selected from the group consisting of hydrogen, halogen, $C_1$-$C_4$ alkyl, $C_2$-$C_4$ alkenyl, $C_2$-$C_4$ alkynyl, trifluoromethyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, $C_1$-$C_4$-alkylamino, N-($C_1$-$C_4$-alkyl)amino, N,N-di($C_1$-$C_4$-alkyl)amino, thiol, $C_1$-$C_4$ alkylthio, $C_1$-$C_4$ alkylsulfonyl, $C_1$-$C_4$ alkylsulfinyl, carboxy, $C_1$-$C_4$ alkoxycarbonyl, and nitro;

one of

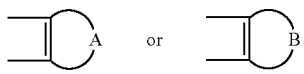

is present and is selected from the group consisting of

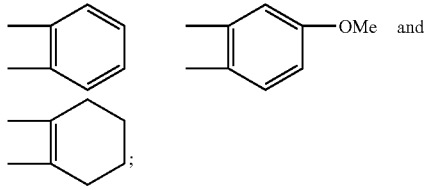

$R^1$ is a $C_1$-$C_7$ alkyl group optionally substituted with at least one substituent selected from the group consisting of halogen, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl; a $C_1$-$C_7$ alkyloxycarbonyl or a substituent of the formula II

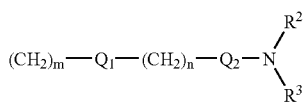

wherein $R^2$ and $R^3$ are each independently selected from the group consisting of hydrogen, $C_1$-$C_4$ alkyl, and aryl or $R^2$ and $R^3$ taken together with the nitrogen atom to which they are attached form a heterocycle or heteroaryl group which is optionally substituted with one or two substituents selected from the group consisting of halogen, $C_1$-$C_4$ alkyl, cyano, nitro, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl;

n is an integer from 0 to 3;

m is an integer from 1 to 3;

$Q_1$ and $Q_2$ are each independently selected from the group consisting of oxygen, sulphur,

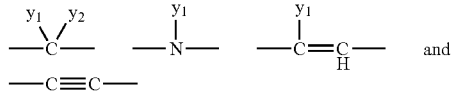

wherein $y_1$ and $y_2$ are each independently selected from the group consisting of hydrogen, halogen, hydroxy, $C_1$-$C_4$ alkoxy, $C_1$-$C_4$ alkanoyl, thiol, $C_1$-$C_4$ alkylthio, $C_1$-$C_4$ alkylsulfonyl, $C_1$-$C_4$ alkylsulfinyl, nitro; a $C_1$-$C_4$ alkyl optionally substituted with at least one substituent selected from the group consisting of halogen atom, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl; and an aryl group optionally substituted with one or two substituents selected from the group consisting of halogen, $C_1$-$C_4$ alkyl, cyano, nitro, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl; or $y_1$ and $y_2$ taken together with the carbon atom to which they are attached form a carbonyl group or an imino group;

and pharmaceutically acceptable salts and solvates thereof.

2. The compound of claim 1, wherein X is S or O.

3. The compound of claim 2, wherein Y and Z are each H.

4. The compound of claim 3, wherein $R^1$ is $CO_2Et$, or $CH_2OH$.

5. The compound of claim 3, wherein $R^1$ is a substituent of formula II.

6. The compound of claim 5, wherein m is 1, n is 1 or 2, $Q_1$ is O and $Q_2$ is $CH_2$.

7. The compound of claim 6, wherein $R^2$ and $R^3$ are each independently H or $CH_3$ or $R^2$ and $R^3$ taken together with the nitrogen atom to which they are attached are morpholine-4-yl, piperidine-1-yl or pyrrolidine-1-yl.

8. The compound of claim 4 selected from the group consisting of:

8-oxa-1-thia-benzo[e]naphtho[3,2-h]azulene-2-carboxylic acid ethyl ester;

1,8-dithia-benzo[e]naphtho[3,2-h]azulene-2-carboxylic acid ethyl ester;

3,10-dithia-benzo[e]naphtho[1,2-h]azulene-2-carboxylic acid ethyl ester;

10-oxa-3-thia-benzo[e]naphtho[1,2-h]azulene-2-carboxylic acid ethyl ester;

11-methoxy-8-oxa-1-thia-benzo[e]naphtho[3,2-h]azulene-2-carboxylic acid ethyl ester;

6,7,8,9-tetrahydro-10-oxa-3-thia-benzo[e]naphtho[1,2-h]azulene-2-carboxylic acid ethyl ester;

10,11,12,13-tetrahydro-8-oxa-1-thia-benzo[e]naphtho[3,2-h]azulene-2-carboxylic acid ethyl ester;

(8-oxa-1-thia-benzo[e]naphtho[3,2-h]azulene-2-yl)-methanol;

(1,8-dithia-benzo[e]naphtho[3,2-h]azulene-2-yl)-methanol;

(3,10-dithia-benzo[e]naphtho[1,2-h]azulene-2-yl)-methanol;

(10-oxa-3-thia-benzo[e]naphtho[1,2-h]azulene-2-yl)-methanol;

(11-methoxy-8-oxa-1-thia-benzo[e]naphtho[3,2-h]azulene-2-yl)-methanol;

(6,7,8,9-tetrahydro-10-oxa-3-thia-benzo[e]naphtho[1,2-h]azulene-2-yl)-methanol; and (10,11,12,13-tetrahydro-8-oxa-1-thia-benzo[e]naphtho[3,2-h]azulene-2-yl)-methanol.

9. The compound of claim 7 selected from the group consisting of:

dimethyl-[2-(8-oxa-1-thia-benzo[e]naphtho[3,2-h]azulene-2-ylmethoxy)-ethyl]-amine;

dimethyl-[3-(8-oxa-1-thia-benzo[e]naphtho[3,2-h]azulene-2-ylmethoxy)-propyl]-amine;

3-(8-oxa-1-thia-benzo[e]naphtho[3,2-h]azulene-2-ylmethoxy)-propylamine;

dimethyl-[3-(1,8-dithia-benzo[e]naphtho[3,2-h]azulene-2-ylmethoxy)-propyl]-amine;

dimethyl-[2-(3,10-dithia-benzo[e]naphtho[1,2-h]azulene-2-ylmethoxy)-ethyl]-amine;

dimethyl-[3-(3,10-dithia-benzo[e]naphtho[1,2-h]azulene-2-ylmethoxy)-propyl]-amine;

dimethyl-[2-(10-oxa-3-thia-benzo[e]naphtho[1,2-h]azulene-2-ylmethoxy)-ethyl]-amine;

dimethyl-[3-(10-oxa-3-thia-benzo[e]naphtho[1,2-h]azulene-2-ylmethoxy)-propyl]-amine;

dimethyl-[3-(11-methoxy-8-oxa-1-thia-benzo[e]naphtho[3,2-h]azulene-2-ylmethoxy)-propyl]-amine;

dimethyl-[2-(6,7,8,9-tetrahydro-10-oxa-3-thia-benzo[e]naphtho[1,2-h]azulene-2-ylmethoxy)-ethyl]-amine;

dimethyl-[3-(6,7,8,9-tetrahydro-10-oxa-3-thia-benzo[e]naphtho[1,2-h]azulene-2-ylmethoxy)-propyl]-amine;

3-(6,7,8,9-tetrahydro-10-oxa-3-thia-benzo[e]naphtho[1,2-h]azulene-2-ylmethoxy)-propylamine;

methyl-[3-(6,7,8,9-tetrahydro-10-oxa-3-thia-benzo[e]naphtho[1,2-h]azulene-2-ylmethoxy)-propyl]-amine;

dimethyl-[2-(10,11,12,13-tetrahydro-8-oxa-1-thia-benzo[e]naphtho[3,2-h]azulene-2-ylmethoxy)-ethyl]-amine;

dimethyl-[3-(10,11,12,13-tetrahydro-8-oxa-1-thia-benzo[e]naphtho[3,2-h]azulene-2-ylmethoxy)-propyl]-amine;

4-[2-(10,11,12,13-tetrahydro-8-oxa-1-thia-benzo[e]naphtho[3,2-h]azulene-2-ylmethoxy)-ethyl]-morpholine;

1-[2-(10,11,12,13-tetrahydro-8-oxa-1-thia-benzo[e]naphtho[3,2-h]azulene-2-ylmethoxy)-ethyl]-piperidine;

1-[2-(10,11,12,13-tetrahydro-8-oxa-1-thia-benzo[e]naphtho[3,2-h]azulene-2-ylmethoxy)-ethyl]-pyrrolidine;

dimethyl-[2-(10,11,12,13-tetrahydro-8-oxa-1-thia-benzo[e]naphtho[3,2-h]azulene-2-ylmethoxy)-propyl]-amine;

dimethyl-[1-methyl-(10,11,12,13-tetrahydro-8-oxa-1-thia-benzo[e]naphtho[3,2-h]azulene-2-ylmethoxy)-ethyl]-amine; and pharmaceutically acceptable salts and solvates thereof.

10. A process for the preparation of a compound of the formula I

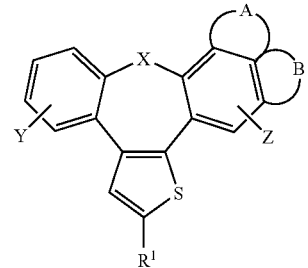

wherein

X is selected from the group consisting of $CH_2$, O, S, $S(=O)$, $S(=O)_2$, and $NR^a$, wherein $R^a$ is hydrogen or a protecting group;

Y and Z are each independently selected from the group consisting of hydrogen, halogen, $C_1$-$C_4$ alkyl, $C_2$-$C_4$ alkenyl, $C_2$-$C_4$ alkinyl, trifluoromethyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, $C_1$-$C_4$ alkylamino, N,N-di($C_1$-$C_4$-alkyl)amino, N,N-di($C_1$-$C_4$-alkyl)amino, thiol, $C_1$-$C_4$ alkylthio, $C_1$-$C_4$ alkylsulfonyl, $C_1$-$C_4$ alkylsulfinyl, carboxy, $C_1$-$C_4$ alkoxycarbonyl, and nitro;

one of

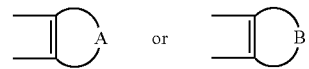

and is selected from the group consisting of

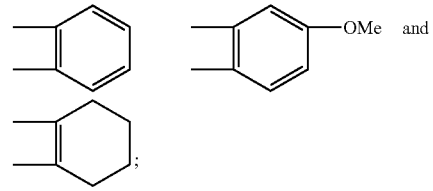

$R^1$ is a $C_1$-$C_7$ alkyl group optionally substituted with at least one substituent selected from the group consisting of halogen, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl; a $C_1$-$C_7$ alkyloxycarbonyl or a substituent of the formula II

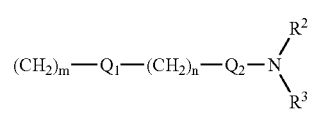

wherein $R^2$ and $R^3$ are each independently selected from the group consisting of hydrogen, $C_1$-$C_4$ alkyl, and aryl or $R^2$ and $R^3$ taken together with the nitrogen atom to which they are attached form a heterocycle or heteroaryl group which is optionally substituted which is optionally substituted with one or two substituents selected from the group consisting of halogen, $C_1$-$C_4$ alkyl, cyano, nitro, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl;

n is an integer from 0 to 3;

m is an integer from 1 to 3;

$Q_1$ and $Q_2$ are each independently selected from the group consisting of oxygen, sulphur,

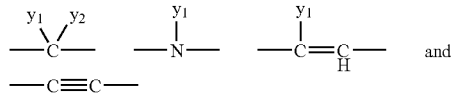

and wherein $y_1$ and $Y_2$ are each independently selected from the group consisting of hydrogen, halogen, hydroxy, $C_1$-$C_4$ alkoxy, $C_1$-$C_4$ alkanoyl, thiol, $C_1$-$C_4$ alkylthio, $C_1$-$C_4$ alkylsulfonyl, $C_1$-$C_4$ alkylsulfinyl, nitro; a $C_1$-$C_4$ alkyl optionally substituted with at least one substituent selected from the group consisting of halogen atom, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl; and an aryl group optionally substituted with one or two substituents selected from the group consisting of halogen, $C_1$-$C_4$ alkyl, cyano, nitro, hydroxy, $C_1$-$C_4$ alkoxy, thiol, $C_1$-$C_4$ alkylthio, amino, N-($C_1$-$C_4$-alkyl)amino, N,N-di($C_1$-$C_4$-alkyl)amino, $C_1$-$C_4$ alkylsulfonyl, and $C_1$-$C_4$ alkylsulfinyl; or $y_1$ and $y_2$ taken together with the carbon atom to which they are attached form a carbonyl group or an imino group;

and pharmaceutically acceptable salts and solvates thereof, which comprises one of the following steps (a) through (e):

a) for a compound of the formula I, wherein $R^1$ is alkyloxycarbonyl, cyclizing a compound of the formula III

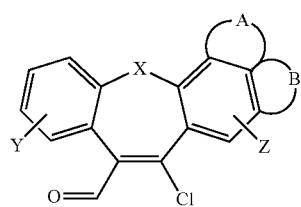

III with an ester of mercaptoacetic acid;

b) for a compound of the formula I, wherein $Q_1$ is —O—, reacting an alcohol of the formula V

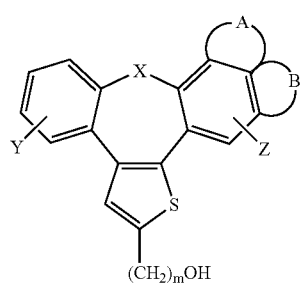

V with a compound of the formula IV

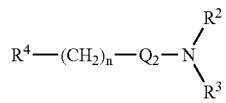

IV wherein $R^4$ is a leaving group;

c) for a compound of the formula I, wherein $Q_1$ is —O—, —NH—, —S— or —C≡C—, reacting a compound of the formula Va

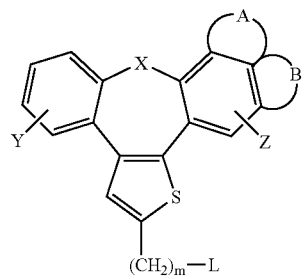

Va wherein L is a leaving group, with a compound of the formula IVa

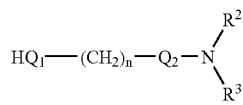

IVa d) for a compound of the formula I, wherein $Q_1$ is —C—, —NH— or —S—, reacting a compound of the formula Vb

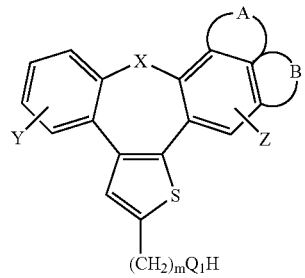

Vb with a compound of the formula IV, wherein $R^4$ is a leaving group; or e) for a compound of the formula I, wherein $Q_1$ is —C=C—, reacting a compound of the formula Vb, wherein $Q_1$ is carbonyl, with a phosphorous ylide.

11. A method of treating inflammation associated with TNF-α comprising administering to a subject in need thereof a compound according to claim 5.

12. The method of claim 11 wherein the inflammation associated with TNF-α is inflammation associated with rheumatoid arthritis.

* * * * *

UNITED STATES PATENT AND TRADEMARK OFFICE
CERTIFICATE OF CORRECTION

PATENT NO. : 7,262,309 B2  Page 1 of 1
APPLICATION NO. : 10/963979
DATED : August 28, 2007
INVENTOR(S) : Mercep et al.

It is certified that error appears in the above-identified patent and that said Letters Patent is hereby corrected as shown below:

Title page should read:
-- (73) Assignee: GlaxoSmithKline Istrazivacki Centar Zagreb, D.O.O. (HR) --

Column 30, line 1 should read:
-- thiol, $C_1$-$C_4$ alkylthio, amino, N-($C_1$-$C_4$-alkyl)amino, --

Column 32, line 22 should read:
-- alkenyl, $C_2$-$C_4$ alkynl, trifluoromethyl, halo-$C_1$-$C_4$ --

Column 32, line 25 should read:
-- lamino, N-($C_1$-$C_4$-alkyl)amino, N,N-di($C_1$-$C_4$- --

Column 32, line 48 should read:
-- lthio, amino, N-($C_1$-$C_4$-alkyl)amino, N,N-di($C_1$-$C_4$- --

Column 34, line 36 should read:
-- d) for a compound of the formula I, wherein Q1 is –O- --

Signed and Sealed this

Twenty-fifth Day of March, 2008

JON W. DUDAS
*Director of the United States Patent and Trademark Office*